United States Patent
Fadli

(10) Patent No.: US 9,364,404 B2
(45) Date of Patent: Jun. 14, 2016

(54) DYE COMPOSITION COMPRISING A CATIONIC O-ALKYL-SUBSTITUTED META-PHENYLENEDIAMINE DERIVATIVE

(71) Applicant: L'OREAL, Paris (FR)

(72) Inventor: Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/422,095

(22) PCT Filed: Aug. 12, 2013

(86) PCT No.: PCT/EP2013/066835
§ 371 (c)(1),
(2) Date: Feb. 17, 2015

(87) PCT Pub. No.: WO2014/026952
PCT Pub. Date: Feb. 20, 2014

(65) Prior Publication Data
US 2015/0202135 A1    Jul. 23, 2015

Related U.S. Application Data

(60) Provisional application No. 61/701,655, filed on Sep. 15, 2012.

(30) Foreign Application Priority Data

Aug. 17, 2012   (FR) ...................... 12 57846

(51) Int. Cl.
| | | |
|---|---|---|
| A61Q 5/10 | (2006.01) | |
| A61K 8/49 | (2006.01) | |
| A61K 8/41 | (2006.01) | |
| C07D 233/60 | (2006.01) | |
| C07C 217/84 | (2006.01) | |
| C07D 207/14 | (2006.01) | |
| C07D 295/088 | (2006.01) | |
| C07D 211/56 | (2006.01) | |
| A61Q 5/06 | (2006.01) | |
| C09B 57/00 | (2006.01) | |

(52) U.S. Cl.
CPC ............... *A61K 8/4913* (2013.01); *A61K 8/411* (2013.01); *A61K 8/49* (2013.01); *A61K 8/494* (2013.01); *A61K 8/4946* (2013.01); *A61Q 5/065* (2013.01); *A61Q 5/10* (2013.01); *C07C 217/84* (2013.01); *C07D 207/14* (2013.01); *C07D 211/56* (2013.01); *C07D 233/60* (2013.01); *C07D 295/088* (2013.01); *C09B 57/00* (2013.01); *A61K 2800/4322* (2013.01); *A61K 2800/4324* (2013.01)

(58) Field of Classification Search
CPC ....... A61Q 5/10; A61K 8/4913; A61K 8/494; A61K 8/4946; A61K 2800/4324; C09B 57/00
USPC ..................................... 8/416, 405
See application file for complete search history.

(56) References Cited

U.S. PATENT DOCUMENTS

| | | |
|---|---|---|
| 4,003,699 A | 1/1977 | Rose et al. |
| 4,125,367 A | 11/1978 | Bugaut et al. |
| RE30,199 E | 1/1980 | Rose et al. |
| 4,259,261 A | 3/1981 | Bugaut et al. |
| 4,329,504 A | 5/1982 | Bugaut et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,099,593 A | 8/2000 | Terranova et al. |
| 6,248,137 B1 | 6/2001 | Terranova et al. |
| 6,284,003 B1 | 9/2001 | Rose et al. |
| 6,338,741 B1 | 1/2002 | Vidal et al. |
| 6,419,711 B1 | 7/2002 | Genet et al. |
| 6,461,389 B1 | 10/2002 | Genet et al. |
| 6,645,258 B2 | 11/2003 | Vidal et al. |
| 6,730,789 B1 | 5/2004 | Birault et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

STIC Search Report dated Jul. 10, 2015.*

(Continued)

*Primary Examiner* — Eisa Elhilo
(74) *Attorney, Agent, or Firm* — The Marbury Law Group, PLLC

(57) ABSTRACT

The invention relates to a meta-phenylenediamine compound of formula (I) below, the addition salts thereof with an acid and the solvates thereof: in which: R represents a hydrogen or halogen atom; a $C_1$-$C_4$ alkyl radical; a carboxyl radical or a ($C_1$-$C_4$) alkoxycarbonyl radical, $R_1$ represents a linear $C_1$-$C_{10}$ alkyl radical substituted with a cationic radical, said alkyl radical being optionally interrupted with one or more oxygen atoms and/or with one or more $NR_6$ groups, said cationic radical being optionally substituted with one or more radicals chosen from $C_1$-$C_4$ alkoxy or $C_1$-$C_4$ (hydroxy)alkyl; $R_6$ represents a hydrogen atom or a linear or branched $C_1$-$C_4$ alkyl radical; An⁻ represents an anion or a mixture of anions which are organic or inorganic and cosmetically acceptable.

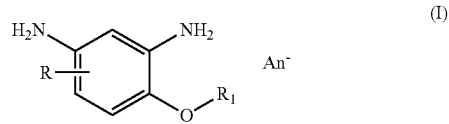

(I)

12 Claims, No Drawings

(56) References Cited

U.S. PATENT DOCUMENTS

| | | |
|---|---|---|
| 6,783,557 B1 | 8/2004 | Terranova et al. |
| 2001/0020310 A1 | 9/2001 | Terranova et al. |
| 2002/0050013 A1 | 5/2002 | Vidal et al. |
| 2002/0144700 A1* | 10/2002 | Lim et al. .................. 132/208 |
| 2003/0019051 A9 | 1/2003 | Vidal et al. |
| 2007/0136959 A1 | 6/2007 | Fadli |
| 2007/0143935 A1 | 6/2007 | Fadli et al. |
| 2010/0115711 A1 | 5/2010 | Fadli et al. |

FOREIGN PATENT DOCUMENTS

| | | |
|---|---|---|
| DE | 4133957 A1 | 4/1993 |
| DE | 19543988 A1 | 5/1997 |
| EP | 0770375 A1 | 5/1997 |
| EP | 0926149 A1 | 6/1999 |
| EP | 1147109 A1 | 10/2001 |
| EP | 1792606 A1 | 6/2007 |
| EP | 1792903 A1 | 6/2007 |
| FR | 2362116 A1 | 3/1978 |
| FR | 2586913 A1 | 3/1987 |
| FR | 2733749 A1 | 11/1996 |
| FR | 2776288 A1 | 9/1999 |
| FR | 2776289 A1 | 9/1999 |
| FR | 2787705 A1 | 6/2000 |
| FR | 2801308 A1 | 5/2001 |
| FR | 2927078 A1 | 8/2009 |
| GB | 1026978 A | 4/1966 |
| GB | 1153196 A | 5/1969 |
| JP | 02-019576 A | 1/1990 |
| JP | 05-163124 A | 6/1993 |
| WO | 94/08960 A1 | 4/1994 |
| WO | 94/08970 A1 | 4/1994 |
| WO | 96/15765 A1 | 5/1996 |
| WO | 97/49378 A1 | 12/1997 |
| WO | 00/43396 A1 | 7/2000 |
| WO | 2004/019897 A1 | 3/2004 |
| WO | 2009/098257 A1 | 8/2009 |

OTHER PUBLICATIONS

International Search Report and Written Opinion for PCT/EP2013/066835, dated Sep. 26, 2013.
English language abstract for EP 0770375 (May 2, 1997).
English language abstract for JP 02-019576 (Jan. 23, 1990).
English language abstract for JP 05-163124 (Jun. 29, 1993).

* cited by examiner

DYE COMPOSITION COMPRISING A CATIONIC O-ALKYL-SUBSTITUTED META-PHENYLENEDIAMINE DERIVATIVE

This is a national stage application of PCT/EP2013/066835, filed internationally on Aug. 12, 2013, which claims priority to U.S. Provisional Application No. 61/701,655, filed on Sep. 15, 2012; as well as French Application 1257846, filed on Aug. 17, 2012.

The invention relates to particular novel cationic meta-phenylenediamine compounds, to a dye composition comprising the latter and also to a dyeing process using these compounds.

It is known practice to dye keratin fibres and in particular human hair with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colour modifiers, the latter being chosen in particular from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" colouring obtained by means of these couplers and oxidation dyes must moreover satisfy a certain number of requirements. Thus, it should have no toxicological drawbacks, it should allow shades to be obtained in the desired intensity, and it should show good resistance to external agents such as light, bad weather, washing, permanent waving treatments, perspiration and rubbing.

The dyes should also allow grey hair to be covered and, finally, they should be as unselective as possible, i.e. they should produce the smallest possible differences in colour along a same keratin fibre, which in general is differently sensitized (i.e. damaged) between its tip and its root.

It is already known practice to use couplers of the meta-phenylenediamine type for dyeing keratin fibres, in particular the hair. Substituted meta-phenylenediamine couplers are, for example, known from document FR 2 362 116. These couplers may have the drawbacks of resulting in colourings that are not sufficiently intense or chromatic and/or that are too selective.

The aim of the present invention is to obtain a hair dye composition that has improved dyeing properties in terms of intensity or chromaticity and/or selectivity and/or resistance to external agents.

Surprisingly and advantageously, the applicant has just discovered a new family of couplers consisting of cationic meta-phenylenediamines. These couplers result in a wide range of colours in oxidation dyeing. They make it possible in particular to expand the colour range while improving the harmlessness of the oxidation dye couplers. Furthermore, these cationic meta-phenylenediamines make it possible to obtain colours having varied shades and that are powerful and chromatic.

A subject of the invention is therefore a meta-phenylenediamine compound of formula (I) below, the addition salts thereof and the solvates thereof:

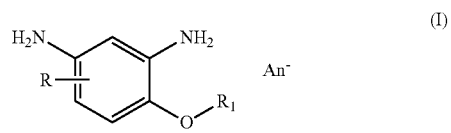

in which:

R represents a hydrogen or halogen atom; a $C_1$-$C_4$ alkyl radical; a carboxyl radical or a ($C_1$-$C_4$) alkoxycarbonyl radical, $R_1$ represents a linear $C_1$-$C_{10}$ alkyl radical substituted with a cationic radical, said alkyl radical being optionally interrupted with one or more oxygen atoms and/or with one or more $NR_6$ groups, said cationic radical being optionally substituted with one or more radicals chosen from hydroxyl, $C_1$-$C_4$ alkoxy or $C_1$-$C_4$ (hydroxy)alkyl and the cationic radical is a linear or branched or heterocyclic radical comprising a quaternary ammonium, this quaternary ammonium being of the type —$N^+RaRbRc$, Ra, Rb and Rc, which may be identical or different, representing a $C_1$-$C_6$ alkyl radical which may be substituted with a hydroxyl, a $C_1$-$C_4$ alkoxy or a $C_1$-$C_4$ (hydroxy)alkyl. Ra and Rb may together form a 5- to 8-membered heterocycle, in which case the Rc radical is a $C_1$-$C_6$ alkyl radical which may be substituted with a hydroxyl radical, a $C_1$-$C_4$ alkoxy radical or a $C_1$-$C_4$ (hydroxy)alkyl radical, said linear cationic radical being chosen from:

triethylammonium, dimethylethylammonium, diisopropylméthylammonium radicals, and mixtures thereof, quaternary ammonium —$N^+RaRbRc$, Ra, Rb and Rc, which may be identical or different, representing a $C_1$-$C_6$ alkyl radical which may be substituted with a hydroxyl, a $C_1$-$C_4$ alcoxy or a $C_1$-$C_4$ (hydroxy)alkyl;

$R_6$ represents a hydrogen atom or a linear or branched $C_1$-$C_4$ alkyl radical;

An$^-$ represents an anion or a mixture of anions which are organic or inorganic and cosmetically acceptable, with the exception of the following compounds:

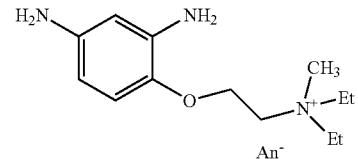

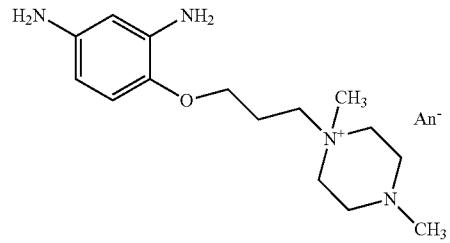

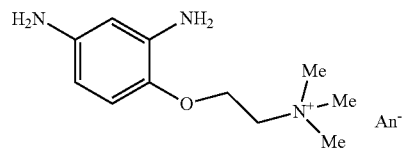

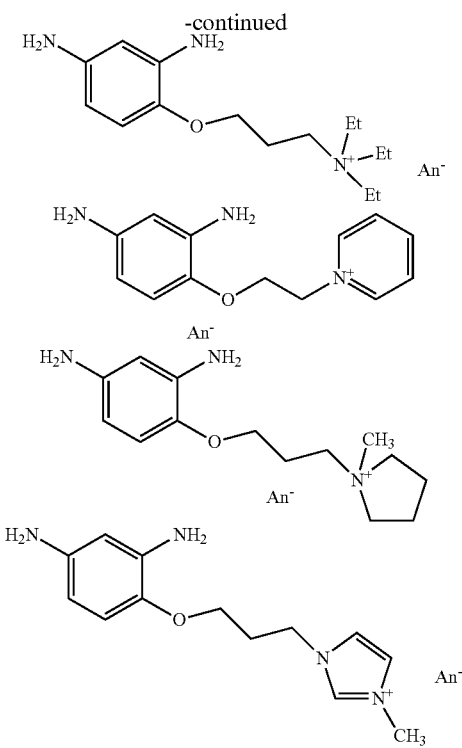

Another subject of the invention is a composition for dyeing keratin fibres comprising, in a suitable dye medium, at least one meta-phenylenediamine compound of formula (I) as defined above. Another subject of the invention is a process for dyeing keratin fibres, consisting in applying this composition to said fibres.

Another subject of the invention is the use of the composition of the present invention for dyeing keratin fibres, in particular human keratin fibres such as the hair.

The invention also relates to multi-compartment devices comprising compositions using one or more couplers chosen from the compound of formula (I) or an addition salt thereof with an acid.

A final subject of the invention is a dyeing kit comprising, on the one hand, a dye composition containing a compound of formula (I) and, on the other hand, a composition containing an oxidizing agent.

The compounds of the present invention make it possible in particular to obtain compositions for dyeing keratin fibres that are suitable for use in oxidation dyeing and that make it possible to obtain a hair colouring that has improved dyeing properties in terms of intensity or chromaticity and/or selectivity and/or resistance to external agents such as shampoo, sweat, permanent reshaping and light.

For the purposes of the present invention, and unless otherwise indicated:
- an "alkyl radical" is a linear or branched $C_1$-$C_{20}$ and preferably $C_1$-$C_8$ hydrocarbon-based radical;
- an "alkenylene radical" is an unsaturated hydrocarbon-based divalent radical as defined previously, which may contain from 1 to 4 conjugated or unconjugated —C=C— double bonds; the alkenylene group particularly contains 1 or 2 unsaturation(s);
- the expression "optionally substituted" attributed to the alkyl radical means that said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming with the nitrogen atom that bears them a 5- to 7-membered heterocycle, optionally comprising another heteroatom identical to or different from nitrogen; v) or a quaternary ammonium group —N$^+$R'R''R''', M$^-$ for which R', R'' and R''', which may be identical or different, represent a hydrogen atom or a $C_1$-$C_4$ alkyl group, or else —N$^+$R'R''R''' forms a heteroaryl such as imidazolium optionally substituted with a $C_1$-$C_4$ alkyl group, and M$^-$ represents the counterion of the corresponding organic acid, inorganic acid or halide;
- an "alkoxy radical" is an alkyl-oxy radical for which the alkyl radical is a linear or branched $C_1$-$C_{16}$ and preferentially $C_1$-$C_8$ hydrocarbon-based radical;
- when the alkoxy group is optionally substituted, this implies that the alkyl group is optionally substituted as defined hereinabove;
- the expression "at least one" is equivalent to "one or more"; and
- the term "inclusive" for a range of concentrations means that the limits of that range are included in the defined range.

It should be noted that, in the text hereinbelow, unless otherwise indicated, the limits of a range of values are included in that range.

Compound of Formula (I)

A subject of the invention is therefore a meta-phenylenediamine compound of formula (I) below, the addition salts thereof and the solvates thereof:

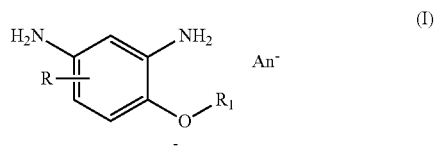

in which:
R represents a hydrogen or halogen atom; a $C_1$-$C_4$ alkyl radical; a carboxyl radical or a ($C_1$-$C_4$) alkoxycarbonyl radical,
$R_1$ represents a linear $C_1$-$C_{10}$ alkyl radical substituted with a cationic radical, said alkyl radical being optionally interrupted with one or more oxygen atoms and/or with one or more $NR_6$ groups, said cationic radical being optionally substituted with one or more radicals chosen from hydroxyl, $C_1$-$C_4$ alkoxy or $C_1$-$C_4$ (hydroxy)alkyl and
the cationic radical is a linear or branched or heterocyclic radical comprising a quaternary ammonium, this quaternary ammonium being of the type —N$^+$RaRbRc, Ra, Rb and Rc, which may be identical or different, representing a $C_1$-$C_6$ alkyl radical which may be substituted with a hydroxyl, a $C_1$-$C_4$ alkoxy or a $C_1$-$C_4$ (hydroxy)alkyl. Ra and Rb may together form a 5- to 8-membered heterocycle, in which case the Rc radical is a $C_1$-$C_6$ alkyl radical which may be substituted with a hydroxyl radical, a $C_1$-$C_4$ alkoxy radical or a $C_1$-$C_4$ (hydroxy)alkyl radical, said linear cationic radical being chosen from: triethylammonium, dimethylethylammonium, diisopropylmethylammonium radicals, and mixtures thereof, quaternary ammonium —N$^+$RaRbRc, Ra, Rb and Rc, which may be identical or different, representing a $C_1$-$C_6$ alkyl radical which may be substituted with a hydroxyl, a $C_1$-$C_4$ alcoxy or a $C_1$-$C_4$ (hydroxy)alkyl;

$R_6$ represents a hydrogen atom or a linear or branched $C_1$-$C_4$ alkyl radical;

An⁻ represents an anion or a mixture of anions which are organic or inorganic and cosmetically acceptable, with the exception of the following compounds:

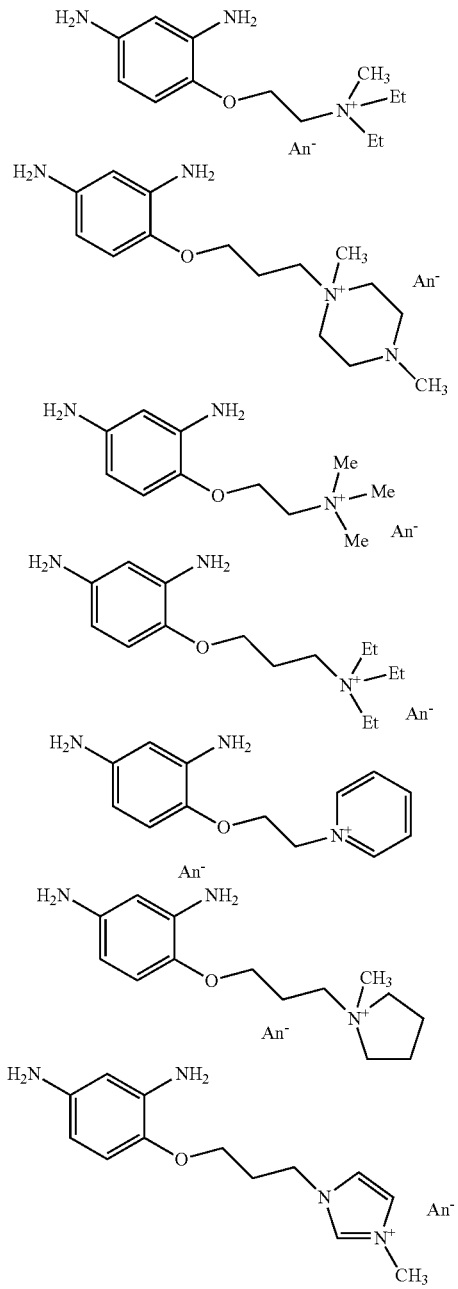

The electroneutrality of the compounds of formula (I) is ensured by an anion or a mixture of anions, labelled An⁻, which are organic or inorganic and are cosmetically acceptable.

An⁻ represents an anion or a mixture of anions chosen, for example, from a halide such as chloride, bromide, fluoride or iodide; a hydroxide; a sulfate; a hydrogen sulfate; an alkylsulfate in which the linear or branched alkyl part is $C_1$-$C_6$, such as the methylsulfate or ethylsulfate ion; carbonates and hydrogen carbonates; salts of carboxylic acids, such as formate, acetate, citrate, tartrate and oxalate; alkyl sulfonates for which the linear or branched alkyl part is $C_1$-$C_6$, such as the methylsulfonate ion; arylsulfonates for which the aryl part, preferably phenyl, is optionally substituted with one or more $C_1$-$C_4$ alkyl radicals, for instance 4-toluylsulfonate; and alkylsulfonyls such as mesylate.

The compounds of general formula (I) may be in free form or in the form of salts, such as addition salts with an inorganic acid preferably chosen from hydrochloric acid, hydrobromic acid, sulfuric acid sulfates and phosphoric acid or with an organic acid such as, for example, citric acid, succinic acid, tartaric acid, lactic acid, 4-toluylsulfonic acid, benzenesulfonic acid, acetic acid, para-toluenesulfonic acid, formic acid and methanesulfonic acid.

The compounds of general formula (I) may also be in the form of solvates, for example a hydrate or a solvate of a linear or branched alcohol such as ethanol or isopropanol.

In the context of the invention, a derivative of formula (I) is understood to mean all mesomeric or isomeric forms.

The compound of formula (I) is a mono cationic compound, the $R_1$ radical being substituted with a single cationic radical In the context of the invention, the expression "cationic radical present in the compound of formula (I)" is understood to mean any linear or branched or heterocyclic radical comprising a quaternary ammonium, this quaternary ammonium being of the type —N⁺RaRbRc, Ra, Rb and Rc, which may be identical or different, representing a $C_1$-$C_6$ alkyl radical which may be substituted with a hydroxyl, a $C_1$-$C_4$ alkoxy or a $C_1$-$C_4$ (hydroxy)alkyl. Ra and Rb may together form a 5- to 8-membered heterocycle, in which case the Rc radical is a $C_1$-$C_6$ alkyl radical which may be substituted with a hydroxyl radical, a $C_1$-$C_4$ alkoxy radical or a $C_1$-$C_4$ (hydroxy)alkyl radical.

When linear, the cationic radical is chosen from triethylammonium, dimethylethylammonium, diisopropylmethylammonium and mixtures thereof.

Preferably, Ra, Rb, Rc, which may be identical or different, represent a $C_1$-$C_2$ alkyl radical, in particular methyl or ethyl, optionally substituted with a hydroxyl radical.

Preferably, when Ra and Rb together form a 5- to 8-membered heterocycle, the Rc radical represents a $C_1$-$C_2$ alkyl radical which may be substituted with a hydroxyl radical, a $C_1$-$C_4$ alkoxy radical or a $C_1$-$C_4$ (hydroxy)alkyl radical.

Thus, the compounds of formula (I) according to the invention carry a permanent cationic charge which is independent of the pH of the medium in which the compounds are formulated.

The term "cationic heterocycle" is understood to mean a 5- to 8-membered heterocycle of which one of the members is a quaternary ammonium or a non-cationic heterocyclic radical substituted with a cationic radical —N⁺RaRbRc, Ra, Rb and Rc, which may be identical or different, representing a $C_1$-$C_6$ alkyl radical that may be substituted with a hydroxyl, $C_1$-$C_4$ alkoxy or $C_1$-$C_4$ (hydroxy)alkyl, and preferably chosen from trimethylammonium, triethylammonium, dimethylethylammonium, diethylmethylammonium, diisopropylmethylammonium, diethylpropylammonium, hydroxyethyldiethylammonium, di-beta-hydroxyethylmethylammonium, di-beta-hydroxyethylethylammonium and tri-beta-hydroxyethylammonium radicals, and mixtures thereof.

By way of example of a cationic heterocycle, mention may be made of imidazolium, pyridinium, piperidinium, piperazinium, pyrrolidinium, morpholinium and pyrimidinium radicals, thiazoliums, benzimidazoliums, benzothiazoliums, oxazoliums, benzotriazoliums, pyrazoliums, triazoliums and benzoxazoliums, these cationic heterocycles being optionally substituted with one or more radicals, which may be identical or different, chosen from a hydroxyl radical, $C_1$-$C_4$ alkoxy radical or $C_1$-$C_4$ (hydroxy)alkyl radical, and mixtures thereof.

By way of example of a cationic heterocycle, mention may also be made of pyrrolidine or piperidine or piperazine radicals, substituted with a cationic —$N^+RaRbRc$ radical, Ra, Rb and Rc, which may be identical or different, representing a $C_1$-$C_6$ alkyl radical which may be substituted with a hydroxyl, a $C_{1-4}$ alkoxy or a $C_1$-$C_4$ (hydroxy)alkyl, and preferably chosen from trimethylammonium, triethylammonium, dimethylethylammonium, diethylmethylammonium, diisopropylmethylammonium, diethylpropylammonium, hydroxyethyldiethylammonium, di-beta-hydroxyethylmethylammonium and tri-beta-hydroxyethylammonium radicals, and in particular the pyrrolidine radical or piperidine radical, substituted with a tri($C_1$-$C_4$)alkyl ammonium radical, and mixtures thereof.

Preferably, the cationic radicals are chosen from triethylammonium, dimethylethylammonium, diisopropylmethylammonium, diethylpropylammonium, hydroxyethyldiethylammonium, di-beta-hydroxyethylmethylammonium, di-beta-hydroxyethylethylammonium, tri-beta-hydroxyethylammonium, imidazolium, pyridinium, piperidinium, piperazinium, pyrrolidinium, morpholinium and pyrimidinium radicals, thiazoliums, benzimidazoliums and benzothiazoliums.

More preferentially, the cationic radicals are chosen from triethylammonium, di-beta-hydroxyethylmethylammonium, di-beta-hydroxyethylethylammonium, tri-beta-hydroxyethylammonium, imidazolium, piperidinium, piperazinium, pyrrolidinium and morpholinium radicals Preferably, in formula (I), R represents a hydrogen atom.

I/ According to a first embodiment of the invention, the compounds of formula (I) are such that:
  R represents a hydrogen atom,
  $R_1$ is a linear $C_2$-$C_8$ alkyl radical, substituted with a cationic quaternary ammonium radical—chosen from triethylammonium, dimethylethylammonium, diisopropylmethylammonium and diethylpropylammonium+radicals, and mixtures thereof.
  According to a second variant, $R_1$ is a linear $C_4$-$C_8$ alkyl radical, substituted with a non-cyclic, cationic quaternary ammonium radical —$N^+RaRbRc$, Ra, Rb and Rc, which may be identical or different, representing a $C_1$-$C_6$ hydoxyalkyl radical substituted with a hydroxyl or $C_1$-$C_4$ (hydroxy)alkyl, preferably with a hydroxyl radical, said cationic radical being preferably chosen from hydroxyethyldiethylammonium, di-beta-hydroxyethylmethylammonium, di-beta-hydroxyethylethylammonium and tri-beta-hydroxyethylammonium radicals, and mixtures thereof II/ According to a second embodiment of the invention, the compounds of formula (I) are such that:
  R represents a hydrogen atom,
  $R_1$ is a saturated linear $C_2$-$C_8$ alkyl radical substituted with a 5- to 8-membered cationic heterocyclic radical of which one of the members is a quaternary ammonium or a non-cationic heterocyclic radical substituted with a cationic radical —$N^+RaRbRc$, Ra, Rb and Rc, which may be identical or different, representing a $C_1$-$C_6$ alkyl radical, said cationic heterocyclic radical being optionally substituted with one or more radicals chosen from hydroxyl, $C_1$-$C_4$ alkoxy or $C_1$-$C_4$ (hydroxy)alkyl, and preferably hydroxyl; said cationic radical being preferably chosen from imidazolium, pyridinium, piperidinium, piperazinium, pyrrolidinium, morpholinium and pyrimidinium radicals, thiazoliums, benzimidazoliums, benzothiazoliums, oxazoliums, benzotriazoliums, pyrazoliums, triazoliums and benzoxazoliums, these cationic heterocycles being optionally substituted with one or more radicals, which may be identical or different, chosen from a hydroxyl radical, a $C_1$-$C_4$ alcoxy radical or a $C_1$-$C_4$ (hydroxy)alkyl radical, and mixtures thereof.

According to a first variant, $R_1$ is a saturated linear $C_2$-$C_8$ alkyl radical substituted with a 5- to 8-membered cationic radical of which one of the members is a quaternary ammonium, preferably chosen from imidazolium, pyridinium, piperidinium, piperazinium, pyrrolidinium, morpholinium and pyrimidinium radicals, thiazoliums, benzimidazoliums, benzothiazoliums, oxazoliums, benzotriazoliums, pyrazoliums, triazoliums and benzoxazoliums, these cationic heterocycles being substituted with one or more radicals, which may be identical or different, chosen from a hydroxyl radical and a $C_1$-$C_4$ (hydroxy)alkyl radical, and mixtures thereof.

According to a second variant, $R_1$ is a saturated linear $C_4$-$C_8$ alkyl radical substituted with a 5- to 8-membered cationic radical of which one of the members is a quaternary ammonium, preferably chosen from imidazolium, pyridinium, piperidinium, piperazinium, pyrrolidinium, morpholinium and pyrimidinium radicals, thiazoliums, benzimidazoliums, benzothiazoliums, oxazoliums, benzotriazoliums, pyrazoliums, triazoliums and benzoxazoliums, these cationic heterocycles being optionally substituted with one or more radicals, which may be identical or different, chosen from a hydroxyl radical and a $C_1$-$C_4$ (hydroxy)alkyl radical, and mixtures thereof.

According to a third variant, $R_1$ is a saturated linear $C_2$-$C_8$ alkyl radical substituted with a radical substituted with a cationic heterocyclic radical chosen from the morpholinium radicals of formula (A) or the pyrimidinium radicals of formula (B) or the piperazinium radicals of formula (C) or the cationic pyrrolidine radicals of formula (D) or the cationic piperidine radicals of formula (E).

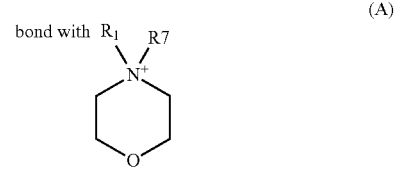

(A)

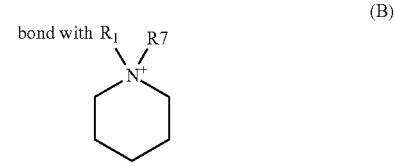

(B)

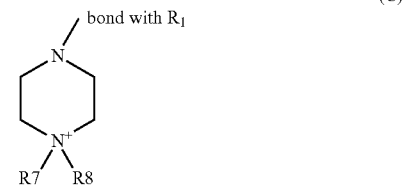

(C)

-continued (D)
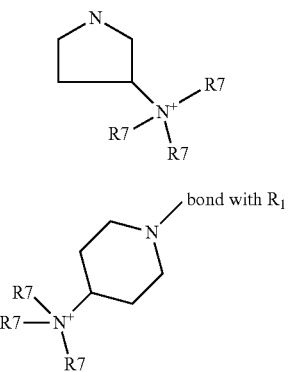
bond with R1

(E)
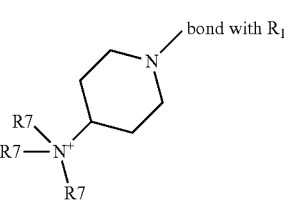
bond with R1 in which R7 and R8 independently denote a $C_1$-$C_4$ alkyl or $C_1$-$C_4$ hydroxyalkyl radical.

Preferably, R7 and R8 denote a $C_1$-$C_4$ alkyl radical and even more preferentially a methyl radical.

Preferably, the cationic meta-phenylenediamines of general formula (I) according to the invention are chosen from the following compounds:

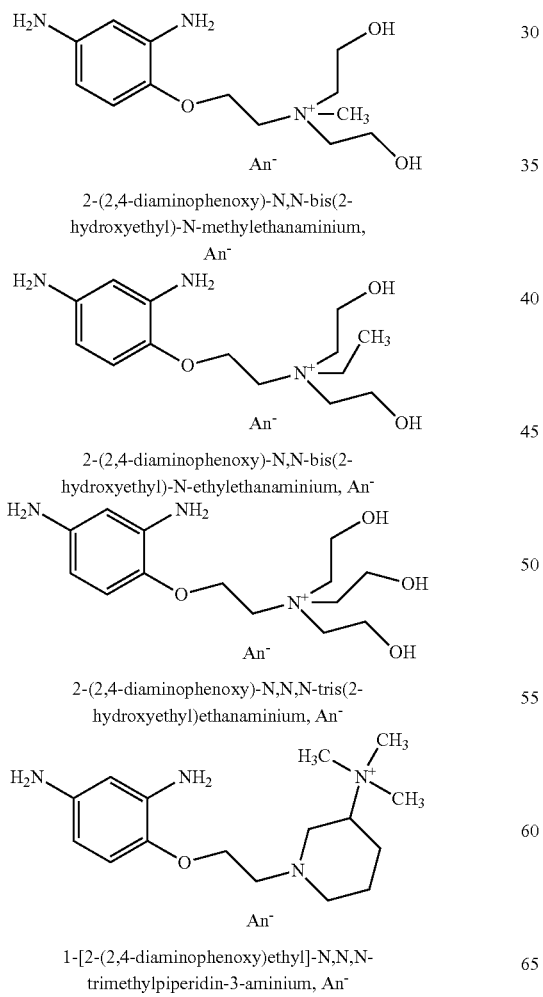

2-(2,4-diaminophenoxy)-N,N-bis(2-hydroxyethyl)-N-methylethanaminium, An⁻

2-(2,4-diaminophenoxy)-N,N-bis(2-hydroxyethyl)-N-ethylethanaminium, An⁻

2-(2,4-diaminophenoxy)-N,N,N-tris(2-hydroxyethyl)ethanaminium, An⁻

1-[2-(2,4-diaminophenoxy)ethyl]-N,N,N-trimethylpiperidin-3-aminium, An⁻

-continued

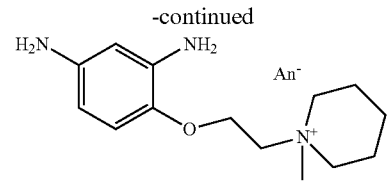

1-[2-(2,4-diaminophenoxy)ethyl]-1-methylpiperidinium, An⁻

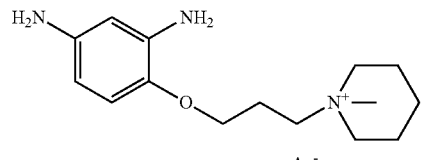

1-[3-(2,4-diaminophenoxy)propyl]-1-methylpiperidinium, An⁻

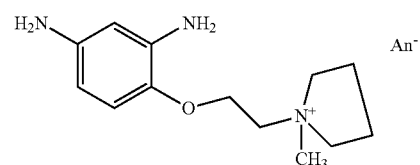

1-[2-(2,4-diaminophenoxy)ethyl]-1-methylpyrrolidinium, An⁻

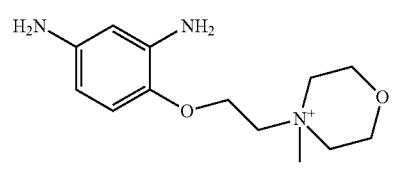

4-[2-(2,4-diaminophenoxy)ethyl]-4-methylmorpholin-4-ium, An⁻

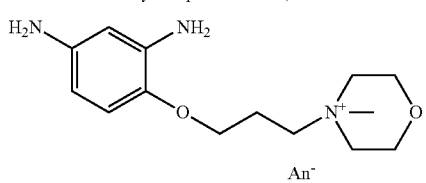

4-[3-(2,4-diaminophenoxy)propyl]-4-methylmorpholin-4-ium, An⁻

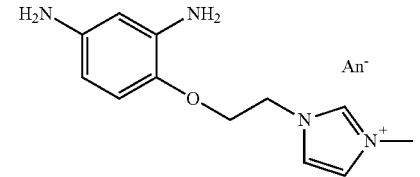

1-[2-(2,4-diaminophenoxy)ethyl]-3-methyl-1H-imidazol-3-ium, An⁻

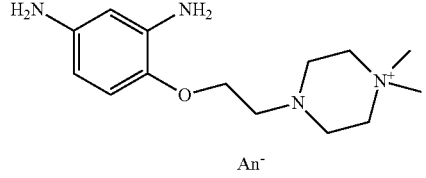

4-[2-(2,4-diaminophenoxy)ethyl]-1,1-dimethylpiperazin-1-ium, An⁻

-continued

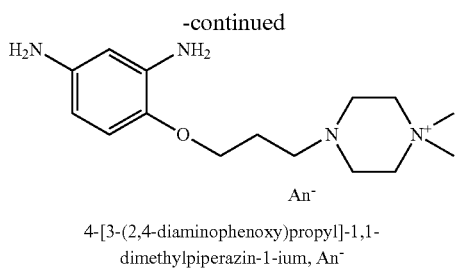

4-[3-(2,4-diaminophenoxy)propyl]-1,1-
dimethylpiperazin-1-ium, An⁻

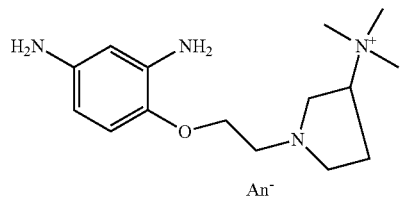

4-[2-(2,4-diaminophenoxy)ethyl]-1,1-
dimethylpiperazin-1-ium, An⁻

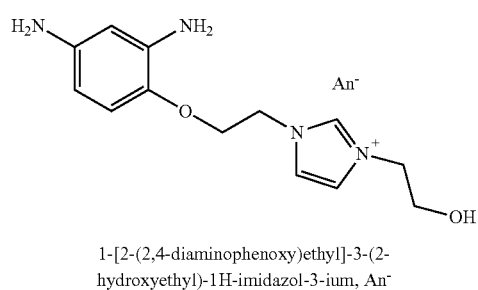

1-[2-(2,4-diaminophenoxy)ethyl]-3-(2-
hydroxyethyl)-1H-imidazol-3-ium, An⁻

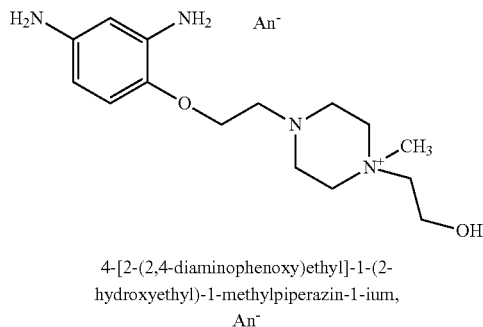

4-[2-(2,4-diaminophenoxy)ethyl]-1-(2-
hydroxyethyl)-1-methylpiperazin-1-ium,
An⁻

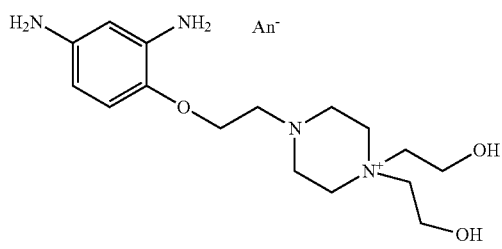

4-[2-(2,4-diaminophenoxy)ethyl]-1,1-
bis(2-hydroxyethyl)-piperazin-1-ium, An⁻

-continued

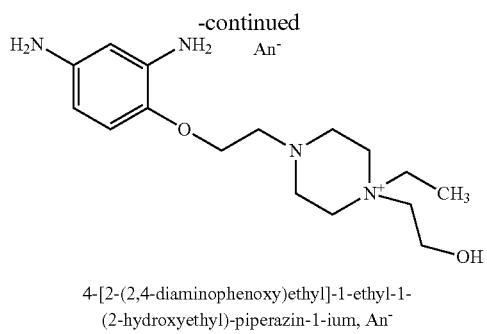

4-[2-(2,4-diaminophenoxy)ethyl]-1-ethyl-1-
(2-hydroxyethyl)-piperazin-1-ium, An⁻ and also the salts and/or solvates or isomers thereof, An⁻ having the same meaning as before.

According to one particularly preferred embodiment, the meta-phenylenediamine compound is chosen from the compounds of formula (I) below, the addition salts thereof and the solvates thereof:

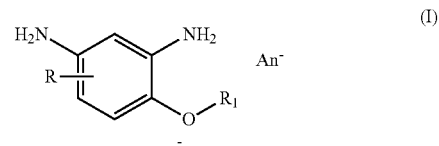

(I)

in which:

R represents a hydrogen or halogen atom; a $C_1$-$C_4$ alkyl radical; a carboxyl radical or a ($C_1$-$C_4$) alkoxycarbonyl radical, $R_1$ represents a linear $C_2$-$C_8$ alkyl radical substituted with a 5- to 8-membered heterocyclic radical of which one of the members is a quaternary ammonium, said heterocycle being preferably substituted with one or more radicals, which may be identical or different, chosen from a $C_1$-$C_4$ (hydroxy)alkyl radical, said heterocycle being preferably chosen from piperazinium, pyrrolidinium, morpholinium and imidazolium radicals substituted with at least one or more $C_1$-$C_4$ alkyl radicals, which may be identical or different, An⁻ represents an anion or a mixture of anions which are organic or inorganic and cosmetically acceptable, with the exception of the following compounds:

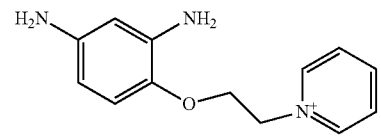

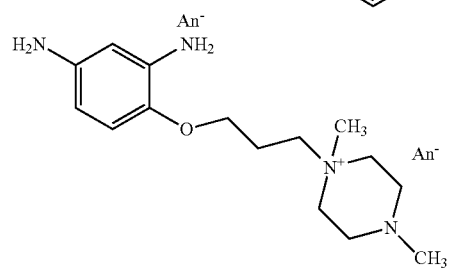

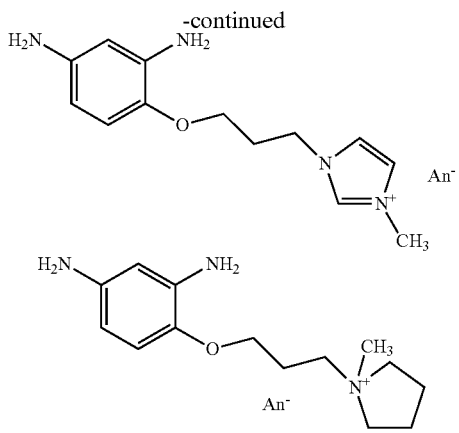

More preferably, the meta-phenylenediamine compound of formula (I) is chosen from 1-[2-(2,4-diaminophenoxy)ethyl]-1-methylpyrrolidinium, An⁻, 1-[2-(2,4-diaminophenoxy)ethyl]-3-methyl-1H-imidazol-3-ium, An⁻, and 4-[2-(2,4-diaminophenoxy)ethyl]-1,1-dimethylpiperazin-1-ium, An⁻, the salts thereof, the solvates thereof, and mixtures thereof.

Dye Composition

Another subject of the invention is a composition for dyeing keratin fibres comprising, in a suitable medium, at least one compound of formula (I) as defined above.

The compound of formula (I) may be present in the composition in an amount of between 0.001% and 10%, preferably between 0.005% and 6%, by weight approximately of the total weight of the dye composition.

The composition may also comprise at least one oxidation base. These bases may in particular be chosen from para-phenylenediamines, bis(phenyl)alkylenediamines, para-aminophenols, ortho-aminophenols and heterocyclic bases, and the addition salts thereof.

Among the para-phenylenediamines, mention may more particularly be made, by way of example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl 3-methylaniline, N,N-bis-(β-hydroxyethyl)-para-phenylenediamine, 4-N,N-bis-(β-hydroxyethyl)amino-2-methylaniline, 4-N,N-bis-(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminopheny-pyrrolidine, 2-thienyl-para-phenylene diamine, 2-βhydroxyethylamino-5-aminotoluene, 3-hydroxy-1-(4'-aminophenyl)pyrrolidine, 6-(4-aminophenylamino)-hexan-1-ol, N-(4-amino-3-methylphenyl)-N-[3-(1H-imidazol-1-yl)propyl]amine, N-(4-aminophenyl)-N-[3-(1H-imidazol-1-yl)propyl]amine and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine, 2-β-acetylaminoethyloxy-para-phenylenediamine, 2-{2-[(4-aminophenyl)amino]ethyl}(2-hydroxyethyl)amino]ethanol and the addition salts thereof with an acid are particularly preferred.

Among the bisphenylalkylenediamines, mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols, mention may be made, by way of example, of para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6-[((5'-amino-2'-hydroxy-3'-methyl)phenyl)methyl]-2-methylphenol, bis[(5'-amino-2'-hydroxy)phenyl-methane and the addition salts thereof with an acid.

Among the ortho-aminophenols, mention may be made, by way of example, of 2-aminophenol, 2-amino-5-methylphenol, 2-amino-6-methylphenol and 5-acetamido-2-aminophenol, and the addition salts thereof with an acid.

Among the heterocyclic bases, mention may be made, by way of example, of pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, 3,4-diaminopyridine, and the addition salts thereof with an acid.

Other pyridine oxidation bases of use in the present invention are the 3-aminopyrazolo[1,5-a]pyridine oxidation bases or the addition salts thereof described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof with an acid.

Among the pyridine bases that are of use in the present invention, mention may also be made of the compounds described in patent applications EP 1792903 and EP 1792606 and the addition salts thereof.

Mention may be made, among pyrimidine derivatives, of the compounds described, for instance, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazolopyrimidine derivatives, mention may be made of the compounds described, for example, in patent applications EP 0847271, EP 0926149 and EP 1147109 and the addition salts thereof.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

By way of oxidation bases, mention may also be made of the diamino-N,N-dihydropyrazolone derivatives of formula (III) or one of the addition salts or solvates thereof:

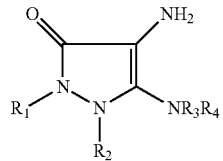

(III)

in which:

$R_1$, $R_2$, $R_3$ and $R_4$, which may be identical or different, represent:
- a linear or branched $C_1$-$C_6$ alkyl radical which is optionally substituted with one or more radicals chosen from the group consisting of a radical $OR_5$, a radical $NR_6R_7$, a carboxyl radical, a sulfonyl radical, a carboxamido radical $CONR_6R_7$, a sulfonamido radical $SO_2NR_6R_7$, a heteroaryl, an aryl optionally substituted with a ($C_1$-$C_4$) alkyl group, a hydroxyl, a $C_1$-$C_2$ alkoxy, an amino, a (di)alkyl($C_1$-$C_2$)amino;
- an aryl radical optionally substituted with one or more ($C_1$-$C_4$)alkyl, hydroxyl, $C_1$-$C_2$ alkoxy, amino or (di)alkyl($C_1$-$C_2$)amino;
- a 5- or 6-membered heteroaryl radical, optionally substituted with one or more radicals chosen from ($C_1$-$C_4$) alkyl and ($C_1$-$C_2$)alkoxy;

$R_3$ and $R_4$ may also represent a hydrogen atom;

$R_5$, $R_6$ and $R_7$ are identical or different and represent a hydrogen atom; a linear or branched $C_1$-$C_4$ alkyl radical which is optionally substituted with one or more radicals chosen from the group consisting of a hydroxyl, a $C_1$-$C_2$ alkoxy, a carboxamido $CONR_8R_9$, a sulfonyl $SO_2R_8$, an aryl optionally substituted with a ($C_1$-$C_4$)alkyl, a hydroxyl, a $C_1$-$C_2$ alkoxy, an amino, a (di)alkyl($C_1$-$C_2$)amino; an aryl optionally substituted with a ($C_1$-$C_4$)alkyl, a hydroxyl, a $C_1$-$C_2$ alkoxy, an amino, a (di)alkyl($C_1$-$C_2$)amino;

$R_6$ and $R_7$ are identical or different and may also represent a carboxamido radical $CONR_8R_9$ or a sulfonyl $SO_2R_8$;

$R_8$ and $R_9$ are identical or different and represent a hydrogen atom or a linear or branched $C_1$-$C_4$ alkyl radical which is optionally substituted with one or more of hydroxyl, $C_1$-$C_2$ alkoxy;

$R_1$ and $R_2$, on the one hand, and $R_3$ and $R_4$, on the other hand, may form, with the nitrogen atoms to which they are attached, a saturated or unsaturated heterocycle containing 5 to 7 members which is optionally substituted with one or more radicals chosen from the group consisting of halogen atoms, amino, (di)alkyl($C_1$-$C_4$)amino, hydroxyl, carboxyl, carboxamido and ($C_1$-$C_2$)alkoxy radicals, $C_1$-$C_4$ alkyl radicals optionally substituted with one or more hydroxyl, amino, (di)alkylamino, alkoxy, carboxyl or sulfonyl radicals;

$R_3$ and $R_4$ may also form, together with the nitrogen atom to which they are attached, a 5- or 7-membered heterocycle in which the carbon atoms may be replaced by an optionally substituted nitrogen or oxygen atom.

These diamino-N,N-dihydropyrazolone derivatives are described in particular in application FR 2866338, and one particularly preferred derivative is 2,3-diamino-6,7-dihydro-1H,5H-pyrazolo[1,2-a]pyrazol-1-one dimethanesulfonate.

Oxidation bases further include diamino-N,N-dihydropyrazolone derivatives having formula (IV) or one of the addition salts or solvates thereof:

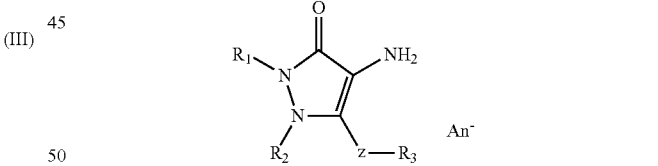

(IV)

in which:

z represents independently:
- a covalent single bond,
- a divalent radical chosen from
- an oxygen atom,
- a radical —$NR_6$—, where $R_6$ represents a hydrogen atom or a $C_1$-$C_6$ alkyl radical, or $R_6$ with $R_3$, together with the nitrogen atom to which they are attached, form a 5- to 8-membered heterocycle which is unsubstituted or substituted, saturated or unsaturated, aromatic or non-aromatic, and optionally contains one or more other heteroatoms or groups chosen from N, O, S, $SO_2$, —CO—, it being possible for the heterocycle to be cationic and/or to be substituted with a cationic radical, a radical —N⁺R₇R₈— where $R_7$ and $R_8$ independently represent an alkyl radical; the alkyl radical may be substituted with an OH or an —Oalkyl, $R_3$ represents:
- a hydrogen
- a $C_1$-$C_{10}$ alkyl radical which is optionally substituted, it being possible for the alkyl radical to be interrupted with a heteroatom or a group chosen from O, N, Si, S, SO and $SO_2$,
- a $C_1$-$C_{10}$ alkyl radical which is substituted and/or interrupted with a cationic radical,
- a halogen,
- an $SO_3H$ radical,
- a 5- to 8-membered ring which is substituted or unsubstituted, saturated or unsaturated or aromatic and optionally contains one or more heteroatoms or groups chosen from N, O, S, $SO_2$, —CO, it being possible for the ring to be cationic and/or to be substituted with a cationic radical, $R_1$ and $R_2$, which may be identical or different, represent:
- a linear or branched $C_1$-$C_6$ alkyl radical which is optionally substituted with one or more radicals chosen from a radical $OR_5$, a radical $NR_9R_{10}$, a carboxyl radical, a sulfonyl radical, a carboxamido radical $CONR_9R_{10}$; a sulfonamido radical $SO_2NR_9R_{10}$, a heteroaryl, an aryl which is optionally substituted with a ($C_1$-$C_4$) alkyl, hydroxyl, $C_1$-$C_2$ alkoxy, amino or (di)alkyl($C_1$-$C_2$)amino group;
- an aryl radical optionally substituted with one or more ($C_1$-$C_4$)alkyl, hydroxyl, $C_1$-$C_2$ alkoxy, amino or (di)alkyl($C_1$-$C_2$)amino;
- a 5- or 6-membered heteroaryl radical which is optionally substituted with one or more radicals chosen from ($C_1$-$C_4$)alkyl which is monosubstituted or polysubstituted with the radical with an OH or an —Oalkyl, ($C_1$-$C_2$)alkoxy;

$R_1$ and $R_2$ may form, with the nitrogen atoms to which they are attached, a saturated or unsaturated heterocycle containing 5 to 7 members which is optionally substituted with one or more radicals chosen from the group consisting of halogen atoms, amino, (di)($C_1$-$C_4$)alkylamino, hydroxyl, carboxyl, carboxamido and ($C_1$-$C_2$)alkoxy radicals, and $C_1$-$C_4$ alkyl radicals which are optionally substituted with one or more hydroxyl, amino, (di)alkylamino, alkoxy, carboxyl or sulfonyl radicals, An⁻ represents an anion or a group of anions making it possible to ensure the electroneutrality of the compounds of formula (IV), on the condition that at least one of the groups Z and $R_3$ represents a cationic radical.

These derivatives of diamino-N,N-dihydropyrazolone are described in patent application FR 2 927 078.

In general, the concentration of the oxidation base(s) ranges from 0.0001% to 20% and preferably from 0.005% to 6% by weight, relative to the total weight of the composition.

Couplers

The dye composition according to the invention may contain and preferably contains one or more additional oxidation couplers, different than the compounds having general formula (I), that are conventionally used for dyeing keratin fibres. Among these couplers, mention may be made in particular of meta-phenylenediamines, meta-aminophenols, meta-diphenols, naphthalene couplers and heterocyclic couplers, and the addition salts thereof.

Examples of a coupler that may be mentioned include 2-methyl-5-aminophenol, 5-N-(β-hydroxyethyl)amino-2-methylphenol, 6-chloro-2-methyl-5-aminophenol, 3-aminophenol, 2,4-dichloro-3-aminophenol, 5-amino-4-chloro-o-cresol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 2,6-dihydroxy-3-4-dimethylpyridine, 3-amino-2-methylamino-6-methoxypyridine, 1-N-(β-hydroxyethyl)amino-3,4-methylenedioxybenzene, 2,6-bis(β-hydroxyethylamino) toluene and 3-methyl-1-phenyl-5-pyrazolone and the addition salts thereof with an acid.

In the dye composition of the present invention, the coupler(s), if it (they) is (are) present, generally represent(s) an amount of between 0.001% and 10% by weight, preferably between 0.005% and 6% by weight approximately of the total weight of the composition.

The dye composition in accordance with the invention may also contain one or more direct dyes that may in particular be chosen from nitrobenzene dyes, azo direct dyes and methine direct dyes. These direct dyes may be of non-ionic, anionic or cationic nature.

The medium that is suitable for dyeing, also known as the dye support, generally comprises water or a mixture of water and one or more solvents, for instance $C_1$-$C_4$ lower alcohols such as ethanol and isopropanol, polyols such as propyleneglycol, dipropyleneglycol or glycerol, and polyol ethers such as dipropyleneglycol monomethylether.

The solvent(s) is (are) generally present in proportions that may be between 1% and 40% by weight approximately and more preferably between 3% and 30% by weight approximately relative to the total weight of the dye composition.

The dye composition in accordance with the invention may also contain various adjuvants conventionally used in hair dye compositions, such as anionic, cationic, non-ionic, amphoteric or zwitterionic surfactants or mixtures thereof, anionic, cationic, non-ionic, amphoteric or zwitterionic polymers or mixtures thereof, inorganic or organic thickeners, and in particular anionic, cationic, non-ionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents customarily used in the dyeing of keratin fibres, or alternatively using standard buffer systems.

Among the acidifying agents, mention made be made, by way of example, of inorganic or organic acids, for instance hydrochloric acid, orthophosphoric acid, sulfuric acid, carboxylic acids, for instance acetic acid, tartaric acid, citric acid and lactic acid, and sulfonic acids.

Among the basifying agents, mention made be made, by way of example, of aqueous ammonia, alkali metal carbonates, alkanolamines, such as mono-, di- and triethanolamines and derivatives thereof, sodium hydroxide, potassium hydroxide and the compounds having formula (III) below:

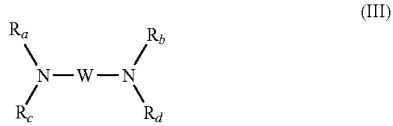

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The composition according to the invention may comprise one or more oxidizing agents.

The oxidizing agents are those conventionally used for the oxidation dyeing of keratin fibres, for example hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The dye composition with or without oxidizing agent according to the invention may be in various forms, such as in the form of liquids, creams or gels, or in any other form that is suitable for dyeing keratin fibres, and in particular human hair.

It may result from the mixing, at the time of use, of several compositions.

In particular, it results from the mixing of at least two compositions, one comprising at least one compound of formula (I), optionally one or more oxidation bases, and optionally one or more additional couplers other than the compounds of formula (I) or salts thereof, and a second composition comprising one or more oxidizing agents as described above.

The composition of the invention is thus applied to the hair for the dyeing of keratin fibres, either as is or in the presence of one or more oxidizing agents for the dyeing of keratin fibres.

The process of the present invention is a process in which the composition according to the present invention as defined previously is applied to the fibres, either alone or in the presence of an oxidizing agent, for a time that is sufficient to develop the desired colouring. The colour may be developed at acidic, neutral or alkaline pH, and the oxidizing agent may be added to the composition of the invention just at the time of use, or it may be used starting from an oxidizing composition which comprises it and which is applied simultaneously with or sequentially to the composition of the invention.

In one particular embodiment, the composition is devoid of oxidizing agent and is mixed, preferably at the time of use, with a composition containing, in a medium appropriate for dyeing, one or more oxidizing agents, these oxidizing agents being present in an amount sufficient to develop a colour. The mixture obtained is then applied to the keratin fibres. After a leave-in time of approximately 3 to 50 minutes, preferably approximately 5 to 30 minutes, the keratin fibres are rinsed, washed with shampoo, rinsed again and then dried.

The oxidizing agents are those indicated above.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably varies between 3 and 12 approximately and more preferably still between 5 and 11. It may be adjusted to the desired value by means of acidifying or basifying agents customarily used in the dyeing of keratin fibres and as defined above.

The ready-to-use composition which is ultimately applied to the keratin fibres may be in a variety of forms, such as in the form of liquids, creams or gels or any other form appropriate for carrying out dyeing of keratin fibres, and in particular of human hair.

Another subject of the invention is a dyeing "kit" or multi-compartment device in which a first compartment contains the dye composition devoid of oxidizing agent of the present invention defined above, comprising one or more oxidation bases chosen from the compound of formula (I) or the addition salts thereof with an acid, and a second compartment contains one or more oxidizing agents.

These devices may be equipped with a means for dispensing the desired mixture on the hair, such as the devices described in patent FR-2 586 913 in the name of the applicant.

Preparation of the Compound of Formula (I)

The synthesis of the compounds of formula (I) can, for example, be carried out according to the following procedures:

General Procedure 1

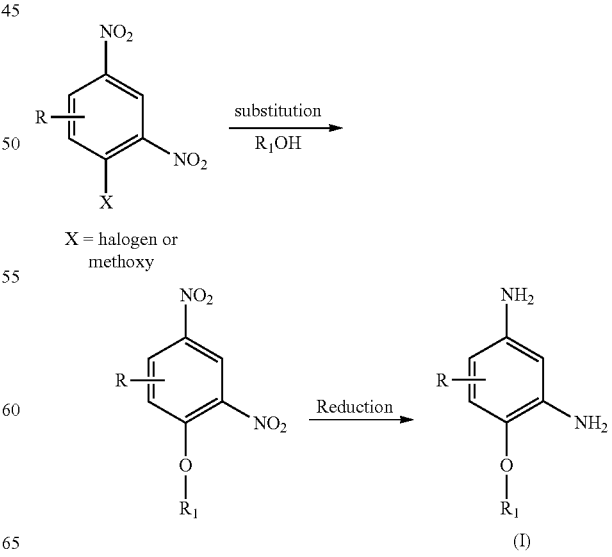

General Procedure 2
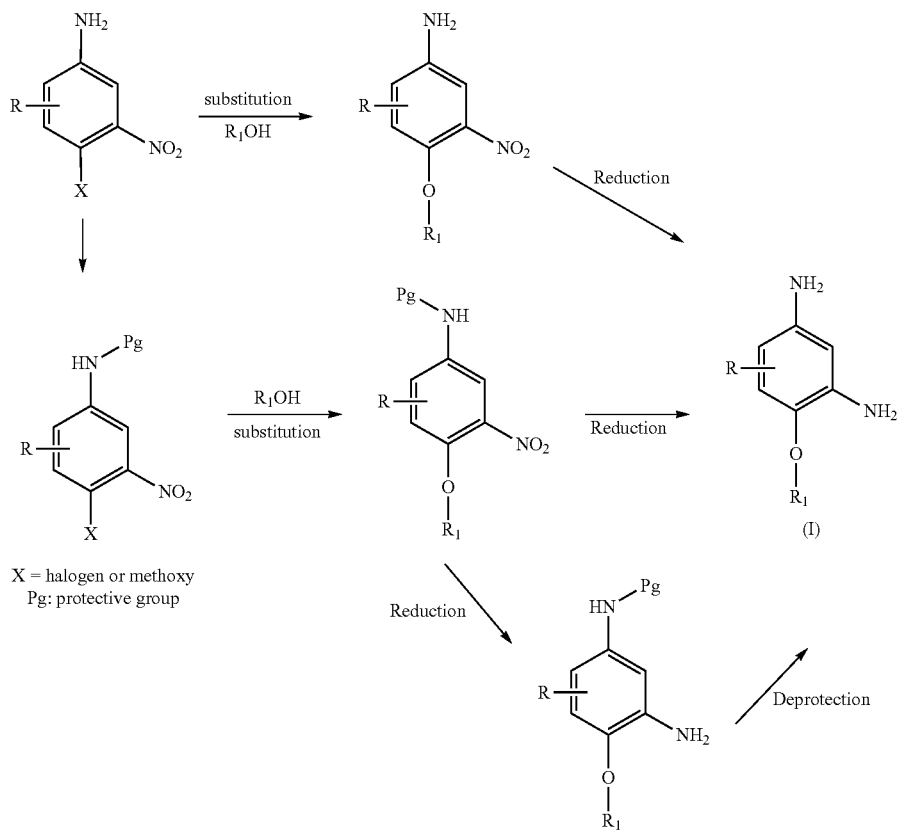
X = halogen or methoxy
Pg: protective group
By way of example, when $R_1$ represents a $C_1$-$C_{10}$ alkyl radical substituted with a cationic radical, said alkyl radical being interrupted with one or more heteroatoms chosen from $NR_2$ or O, then the method of synthesis used may be the following:
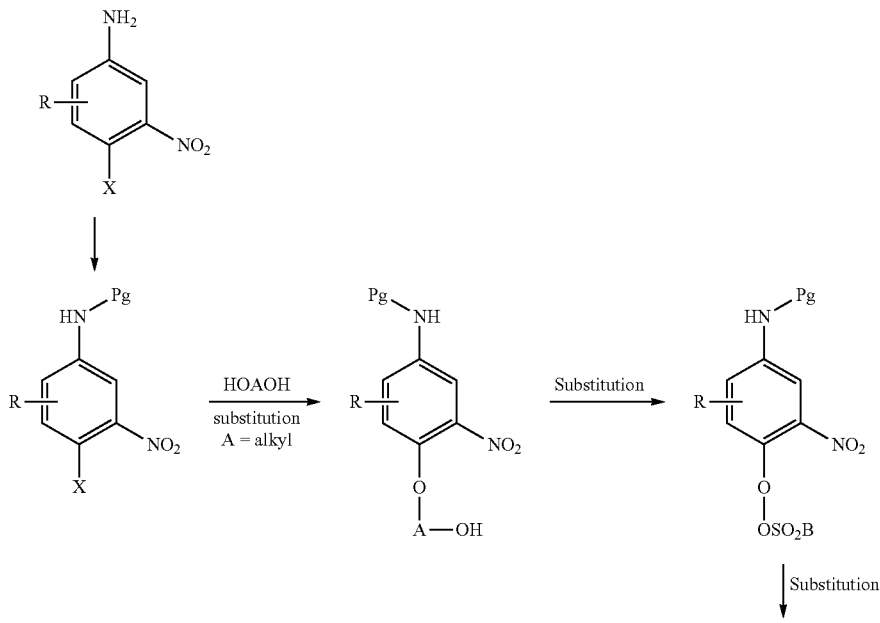

-continued
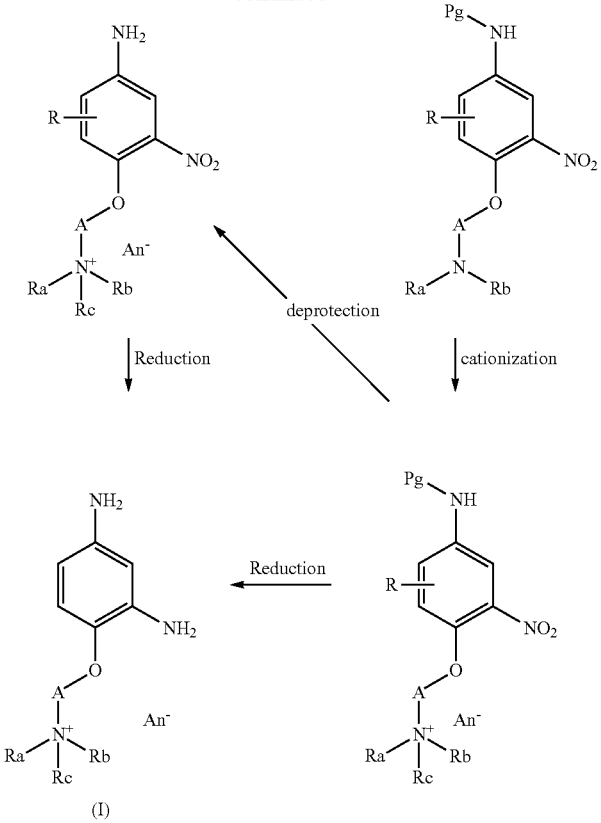
(I)
X = halogen or methoxy
Pg: protective group
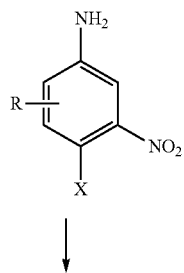
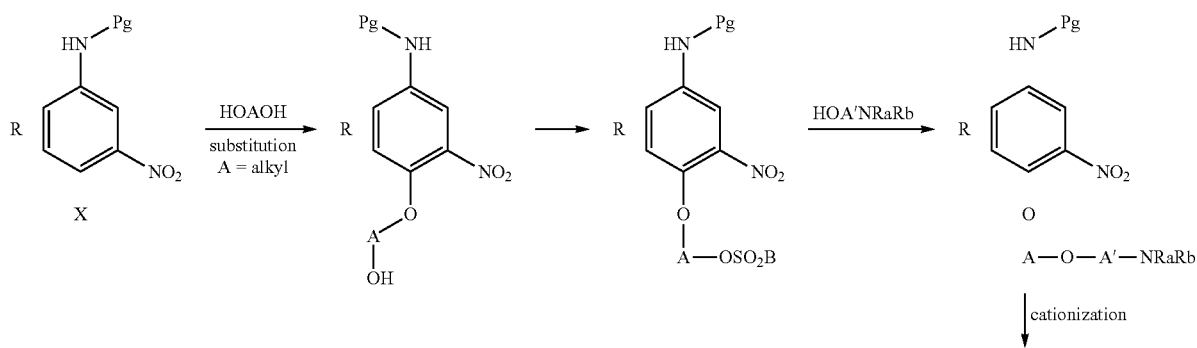

-continued
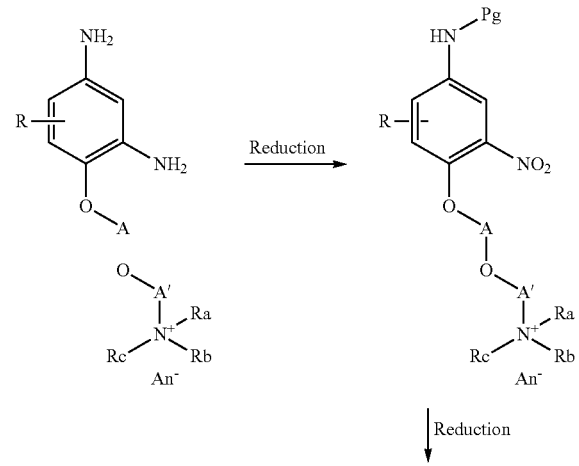
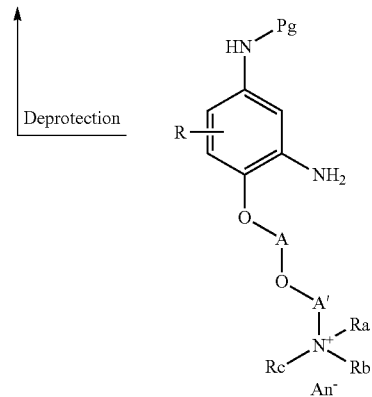
X = halogen or methoxy
Pg: protective group
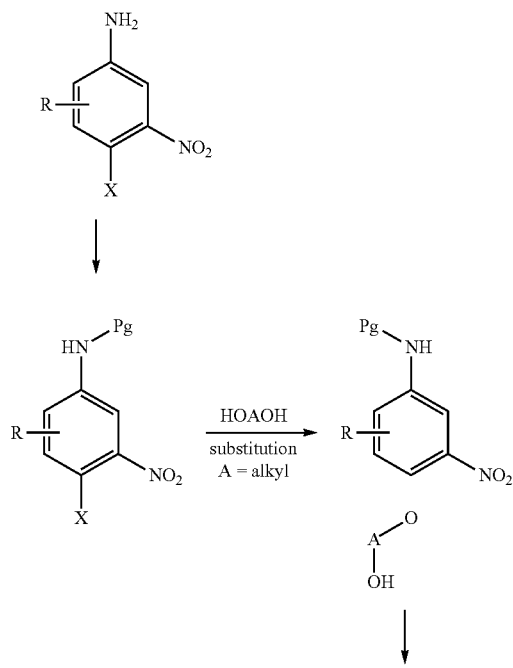

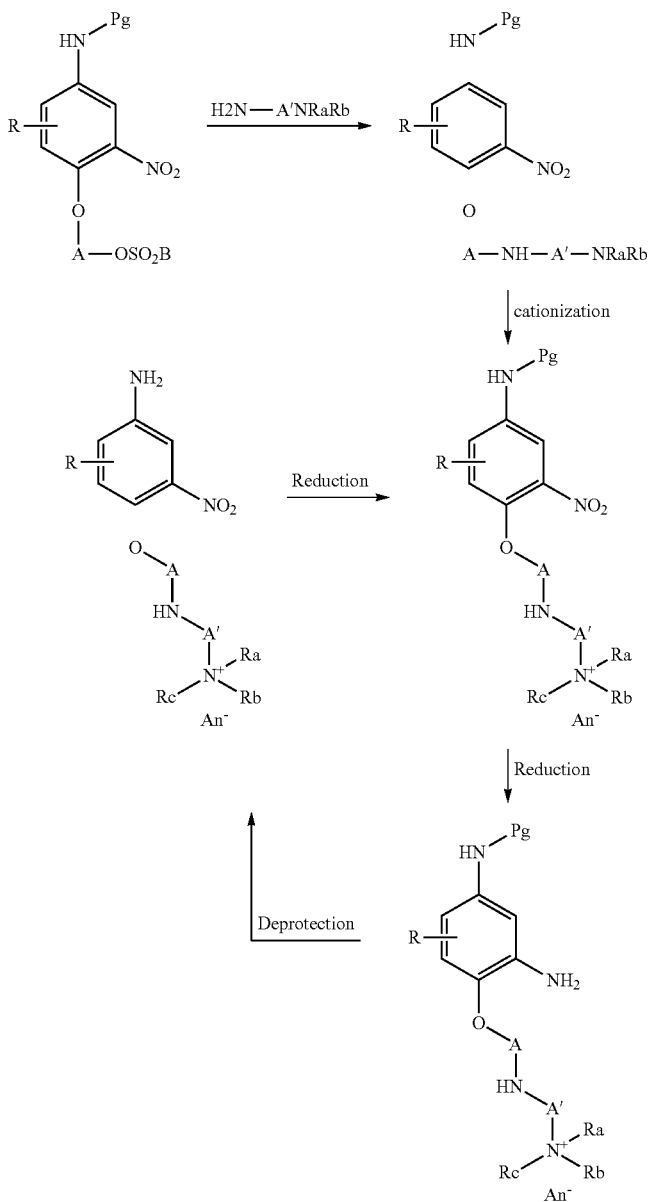

The substitution reaction is performed in a dipolar solvent such as acetonitrile, THF or in DMF or NMP, or in an alcohol such as ethanol for example, in the presence of a base such as triethylamine, ethyldiisopropylamine, sodium hydroxide or potassium hydroxide, for example, and one or more HOAZ1H for 1 to 24 H at a temperature from 20° C. to the reflux temperature of the solvent.

The hydroxyl function thus introduced is then substituted with a halide (for example mesyl or tosyl halide) in a solvent such as acetonitrile or THF or in an alcohol such as ethanol, for example, in the presence of a base such as triethylamine, ethyldiisopropylamine, sodium hydroxide or potassium hydroxide, for example, for 1 to 24 H at a temperature from 20° C. to the reflux temperature of the solvent.

The substitution of the leaving group introduced in the preceding step is performed either by reaction with an aromatic tertiary amine such as methylimidazole to lead directly to the cationic compounds, or by reaction with a particular primary or secondary amine, for instance N,N-dimethylethylenediamine or 2-piperidin-1-ylethanamine to lead to the compounds that are alkylated with at least one equivalent of alkyl halide or methyl sulfate in a solvent such as THF or acetonitrile or dioxane or ethyl acetate for 15 min to 24 H at a temperature ranging from 15° C. to the reflux temperature of the solvent, to give the cationic nitro compounds.

The nitro group of these compounds is reduced under standard conditions, for instance by performing a hydrogenation reaction under heterogeneous catalysis in the presence of Pd/C, Pd(II)/C, Ni/Ra, etc., or alternatively by performing a reduction reaction with a metal, for instance with zinc, iron, tin, etc. (see *Advanced Organic Chemistry*, 3rd Edition, J. March, 1985, Wiley Interscience and *Reduction in Organic Chemistry*, M. Hudlicky, 1983, Ellis Horwood Series Chemical Science).

The examples which follow serve to illustrate the invention without, however, exhibiting a limiting nature.

EXAMPLES

Synthesis Example

Example 1

Synthesis of 1-[2-(2,4-diaminophenoxy)ethyl]-1-methylpyrrolidinium chloride dihydrochloride

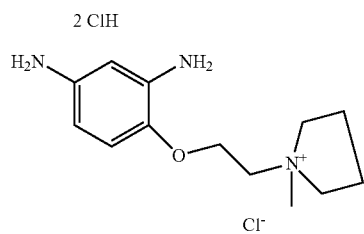 [SMILES: C[N+]1(CCOc2ccc(N)cc2N)CCCC1 ; [Cl-]]

Synthesis of 1-[2-(2,4-dinitrophenoxy)ethyl]pyrrolidine

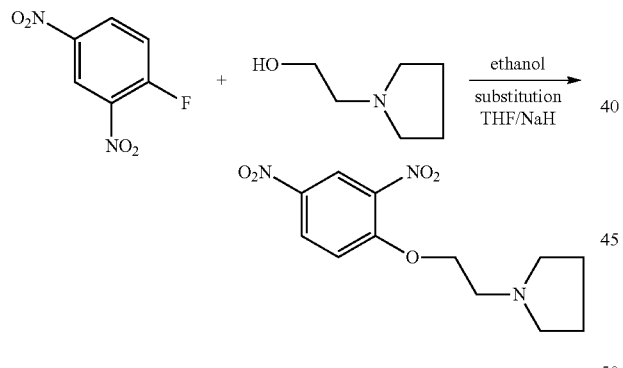

A 250 ml three-necked flask equipped with a thermometer, a condenser, a bubble counter and a dropping funnel, and with magnetic stirring, is charged with 70 ml of THF and 7.66 g (64.48 mmol) of 2-(pyrrolidin-1-yl)ethanol, and the solution is cooled to zero degrees. 2.56 g (64.48 mmol) of sodium hydride are then gently added at this temperature and the stirring is maintained at zero degrees for 1 hour.

A solution of 10 g (53.73 mmol) of 1-fluoro-2,4-dinitrobenzene in 70 ml of THF, cooled beforehand to zero degrees, is then added dropwise.

The reaction is monitored by TLC, elution being carried out with MeOH/CH$_2$Cl$_2$.

After stirring overnight at ambient temperature, the solvent is eliminated by evaporation under vacuum until a solid is obtained which, via purification by silica column flash chromatography (CH$_2$Cl$_2$/MeOH) gives, after evaporation of the solvent, 10.4 g of a yellow solid with a mass (56.8% yield) corresponding to the expected compound.

Synthesis of 1-[2-(2,4-dinitrophenoxy)ethyl]-1-methylpyrrolidinium methyl sulfate

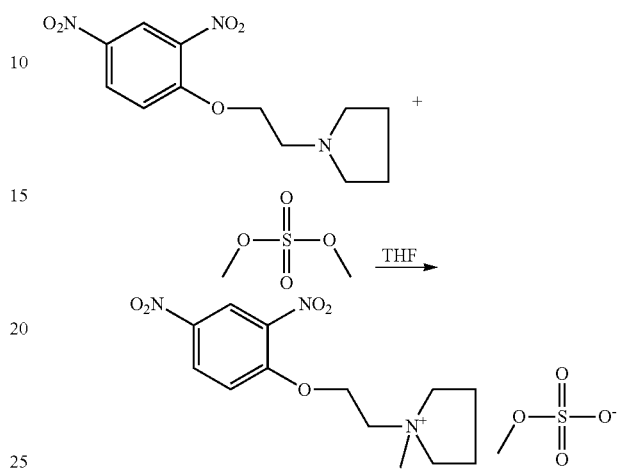

A 100 ml three-necked flask equipped with a thermometer, a condenser, a bubble counter and a dropping funnel, and with magnetic stirring, is charged successively with 40 ml of THF and 5 g (17.78 mmol) of 1-[2-(2,4-dinitrophenoxy)ethyl]pyrrolidine. Added dropwise to this solution are 1.8 ml (18.67 mmol) of dimethyl sulfate and the whole mixture is kept stirring at ambient temperature overnight.

The yellow solid formed is filtered off on a sintered glass funnel, drained by suction, washed with THF and then dried under vacuum at 50° C. in the presence of a desiccant, to constant weight. 5.5 g (76% yield) of the expected compound are thus isolated in the form of a yellow solid.

Mass spectrometry analysis confirms the structure of the expected compound. The expected cation $[C_{13}H_{18}N_3O_5]^+$ is mainly detected.

Synthesis of 1-[2-(2,4-diaminophenoxy)ethyl]-1-methylpyrrolidinium chloride dihydrochloride

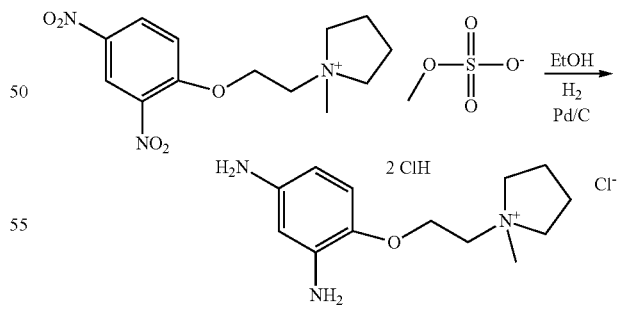

The reduction is carried out by hydrogenation in an apparatus of H-Cube type containing a 90×4 mm cartridge of 10% Pd/C.

A solution of 1 g of 1-[2-(2,4-dinitrophenoxy)ethyl]-1-methylpyrrolidinium methyl sulfate in 100 ml of methanol is introduced under a flow rate of 10 ml per minute through a cartridge of palladium-on-carbon catalyst within an H-Cube system.

On leaving the apparatus, the expected compound is isolated by precipitation from 50 ml of 6N hydrochloric acid in isopropanol.

The solution obtained is brought to 60° C. for one and, after cooling to ambient temperature, the yellow-beige solid formed is filtered off on a No. 4 sintered glass funnel and washed with hydrochloric acid in isopropanol.

After drying under vacuum at 30° C. in the presence of a desiccant, 0.7 g (100% yield) of pink powder corresponding to the expected compound is obtained.

The NMR ($^1$H 400 MHz and $^{13}$C 100.61 MHz DMSO-$d_6$) and mass spectrometry analyses are in accordance with the expected structure.

The expected cation $C_{13}H_{22}N_3O$ is mainly detected.

Example 2

Synthesis of 4-[2-(2,4-diaminophenoxy)ethyl]-1,1-dimethylpiperazin-1-ium chloride trihydrochloride

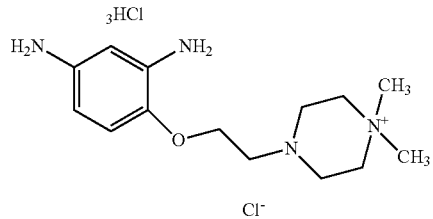 [SMILES: C[N+]1(C)CCN(CCOc2ccc(N)cc2N)CC1 ; [Cl-]]

Synthesis of 1-[2-(2,4-dinitrophenoxy)ethyl]-4-methylpiperazine

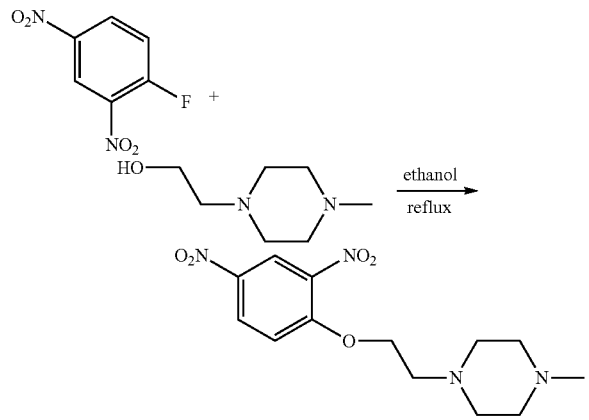

A 250 ml three-necked flask equipped with a thermometer, a condenser, a bubble counter and a dropping funnel, and with magnetic stirring, is charged with 60 ml of THF and 7.9 g (50.94 mmol) of 2-(4-methylpiperazin-1-yl)ethanol. The solution obtained is cooled to zero degrees and 2.04 g (50.94 mmol) of sodium hydride are gently added at this temperature. Stirring is continued at zero degrees for 1 hour.

A solution of 7.9 g (42.45 mmol) of 1-fluoro-2,4-dinitrobenzene and of 70 ml of THF, cooled beforehand to zero degrees, is then added dropwise to the previous medium.

The reaction is monitored by TLC, elution being carried out with MeOH/CH$_2$Cl$_2$.

After stirring overnight at ambient temperature, the solvent is eliminated by evaporation under vacuum until a brown-yellow solid is obtained which, via purification by silica column flash chromatography (CH$_2$Cl$_2$/MeOH) gives, after evaporation of the solvent, a brown solid with a mass of 8.39 g (63.7% yield) corresponding to the expected compound.

Synthesis of 4-[2-(2,4-dinitrophenoxy)ethyl]-1,1-dimethylpiperazin-1-ium methyl sulfate

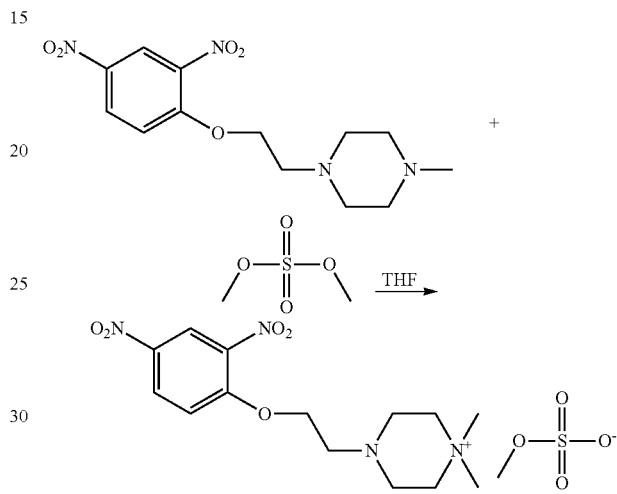

A 100 ml three-necked flask equipped with a thermometer, a condenser, a bubble counter and a dropping funnel, and with magnetic stirring, is charged successively with 50 ml of THF and 8.34 g (26.88 mmol) of 1-[2-(2,4-dinitrophenoxy)ethyl]-4-methylpiperazine.

Added dropwise to this solution are 5.20 ml (53.75) of dimethyl sulfate and the whole mixture is kept stirring at ambient temperature overnight.

The yellow solid formed is filtered off on a sintered glass funnel, drained by suction, washed with THF and then dried under vacuum at 50° C. in the presence of a desiccant, to constant weight. 9.56 g (78.8% yield) of the expected compound are thus isolated in the form of a yellow solid.

Mass spectrometry analysis confirms the structure of the expected compound. The expected cation $[C_{14}H_{21}N_4O_5]^+$ is mainly detected.

Synthesis of 4-[2-(2,4-diaminophenoxy)ethyl]-1,1-dimethylpiperazin-1-ium chloride trihydrochloride

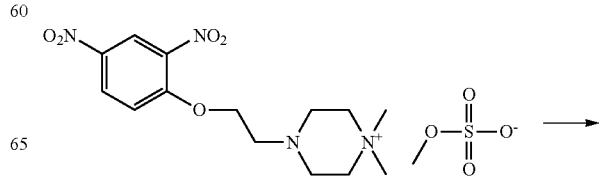

-continued

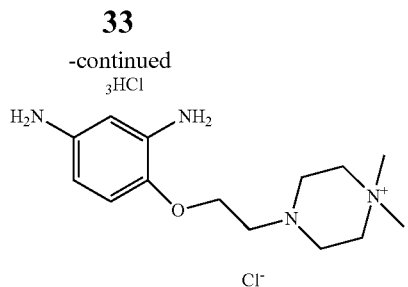

The reduction is carried out by hydrogenation in an apparatus of H-Cube type containing a 90×4 mm cartridge of 10% Pd/C.

A solution of 8 g of 4-[2-(2,4-dinitrophenoxy)ethyl]-1,1-dimethylpiperazin-1-ium methyl sulfate in 800 ml of methanol is introduced under a flow rate of 10 ml per minute through a cartridge of palladium-on-carbon catalyst within an H-Cube system.

On leaving the apparatus, the expected compound is isolated by precipitation from 400 ml of 6N hydrochloric acid in isopropanol.

The solution obtained is brought to 60° C. for one hour and, after cooling to ambient temperature, the pale pink solid formed is filtered off on a No. 4 sintered glass funnel and washed with hydrochloric acid in isopropanol.

After drying under vacuum at 30° C. in the presence of a desiccant, 5.8 g (72.8% yield) of pinkish white powder corresponding to the expected compound are obtained.

The NMR ($^1$H 400 MHz and $^{13}$C 100.61 MHz DMSO-$d_6$) and mass spectrometry analyses are in accordance with the expected structure.

The expected cation $C_{14}H_{25}N_4O$ is mainly detected.

Example 3

Synthesis of 1-[2-(2,4-diaminophenoxy)ethyl]-3-methyl-1H-imidazol-3-ium chloride dihydrochloride

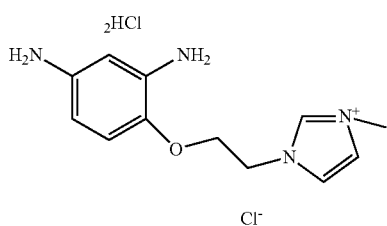 [SMILES: C[n+]1ccn(CCOc2ccc(N)cc2N)c1 ; [Cl-]]

Synthesis of 2-(2,4-dinitrophenoxy)ethyl methanesulfonate

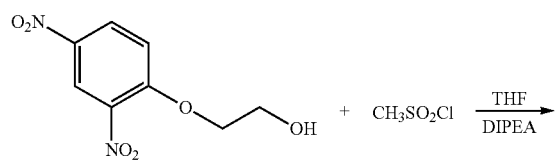

-continued

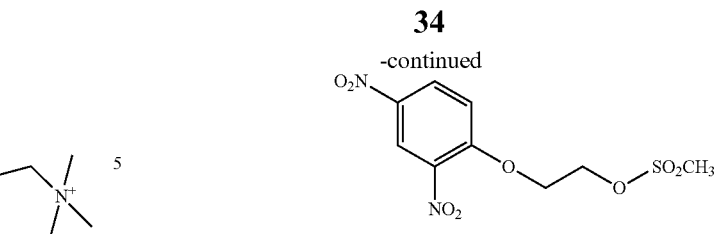

A 250 ml three-necked flask equipped with a thermometer, a condenser, a bubble counter and a dropping funnel, and with magnetic stirring, is charged successively with 90 ml of THF, 10 g (43.83 mmol) of 2-(2,4-dinitrophenoxy)ethanol and 8.87 g (52.26 mmol) of diisopropylethylamine.

Added dropwise to this solution are 4.07 ml (52.59 mmol) of mesyl chloride and the whole mixture is kept stirring at ambient temperature overnight.

The solid formed is isolated by filtration and is purified on a silica column so as to obtain, after drying under vacuum at 50° C. in the presence of a desiccant, to constant weight, 9.5 g (71% yield) of yellow solid corresponding to the expected compound.

Mass spectrometry analysis confirms the structure of the expected compound, $C_9H_{10}N_2O_8S$ corresponding to the expected compound.

Synthesis of 1-[2-(2,4-dinitrophenoxy)ethyl]-3-methyl-1H-imidazol-3-ium methanesulfonate methyl sulfate

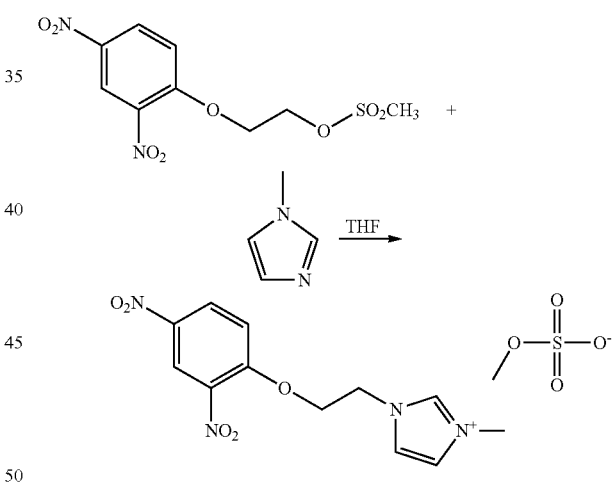

A 100 ml three-necked flask equipped with a thermometer, a condenser, a bubble counter and a dropping funnel, and with magnetic stirring, is charged successively with 30 ml of THF, 230 ml of chloromethane, 8 g (26.12 mmol) of 2-(2,4-dinitrophenoxy)ethyl methanesulfonate and 2.6 g (31.34 mmol) of methylimidazole.

The medium is heated at reflux for 36 hours, the solvent is eliminated by evaporation under vacuum and the viscous solid obtained is taken up with ethanol, with stirring for 4 hours.

A yellow solid forms and is filtered off on a sintered glass funnel, drained by suction, washed with ethanol and then dried under vacuum at 50° C. in the presence of a desiccant, to constant until the weight. 5.75 g (75% yield) of the expected compound are thus isolated in the form of a yellow solid.

Mass spectrometry analysis confirms the structure of the expected compound. The expected cation $[C_{12}H_{13}N_4O_5]^+$ is mainly detected.

Synthesis of 1-[2-(2,4-diaminophenoxy)ethyl]-3-methyl-1H-imidazol-3-ium chloride dihydrochloride

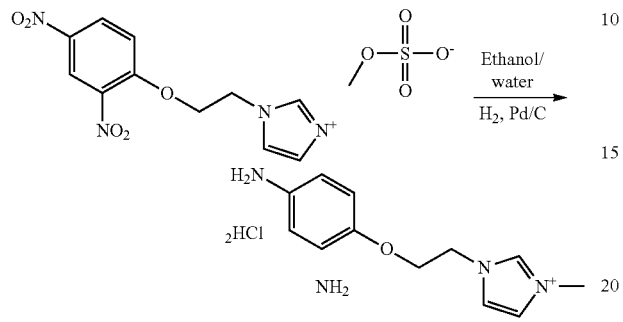

The *reduction is carried out by hydrogenation in an apparatus of HCube type containing a* 90×4 mm cartridge of 10% Pd/C.

A solution of 5.75 g (14.81 mmol) of 1-[2-(2,4-dinitrophenoxy)ethyl]-3-methyl-1H-imidazol-3-ium methanesulfonate in 90 ml of ethanol and 10 ml of water is introduced under a flow rate of 1 ml per minute through a cartridge of palladium-on-carbon catalyst within the H-Cube system.

On leaving the apparatus, the expected compound is isolated by precipitation from 400 ml of 6N hydrochloric acid in isopropanol.

The solution obtained is brought to 60° C. for one hour and, after cooling to ambient temperature, the beige solid formed is filtered off on a No. 4 sintered glass funnel and washed with hydrochloric acid in isopropanol.

After drying under vacuum at 30° C. in the presence of a desiccant, 3.4 g (67% yield) of beige solid corresponding to the expected compound are obtained.

The NMR ($^1$H 400 MHz and $^{13}$C 100.61 MHz DMSO-$d_6$) and mass spectrometry analyses are in accordance with the expected structure.

The expected cation $C_{12}H_{17}N_4O$ is mainly detected.

Examples of Dyeing:

The following dye compositions are prepared:

| | | | |
|---|---|---|---|
| 4-(2,4-diaminophenyl)-1,1-dimethylpiperazin-1-ium chloride dihydrochloride | $10^{-3}$ mol | | |
| 2,3-diamino-6,7-dihydro-1H,5H-pyrazolo[1,2-a]pyrazol-1-one dimethanesulfonate | $10^{-3}$ mol | | |
| 2-[(3-aminopyrazolo[1,5-a]pyridin-2-yl)oxy]ethanol hydrochloride | | $10^{-3}$ mol | |
| 4-(3-aminopyrazolo[1,5-a]pyridin-2-yl)-1,1-dimethylpiperzin-1-ium chloride hydrochloride | | | $10^{-3}$ mol |
| Dye support (1) | () | () | (**) |
| Demineralized water qs | 100 g | 100 g | 100 g |
| Shade observed | Coppery red | Purple mahogany | blue grey green |

(**) dye support (1) pH 9.5

| | |
|---|---|
| 96° ethyl alcohol | 20.8 g |
| 35% aqueous sodium metabisulfite solution | 0.23 g AM |
| Pentasodium salt of diethylenetriaminepentaacetic acid as an aqueous 40% solution | 0.48 g AM |
| C8-C10 alkyl polyglucoside as an aqueous 60% solution | 3.6 g AM |
| Benzyl alcohol | 2.0 g |
| Polyethylene glycol containing 8 units of ethylene oxide | 3.0 g |
| NH$_4$Cl | 4.32 g |
| Aqueous ammonia containing 20% NH$_3$ | 2.94 g |

At the time of use, each composition is mixed with an equal weight of 20-volumes oxygenated water (6% by weight). A final pH of 9.5 is obtained.

Each mixture obtained is applied to locks of grey hair containing 90% white hairs. After a leave-in time of 30 minutes, the locks are rinsed, washed with a standard shampoo, rinsed again and then dried, to give the shades mentioned.

The invention claimed is:

1. A meta-phenylenediamine compound chosen from formula (I), the addition salts thereof and the solvates thereof:

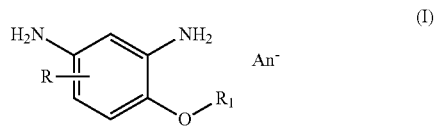

wherein:

R is chosen from a hydrogen or halogen atom; a $C_1$-$C_4$ alkyl radical; a carboxyl radical and a ($C_1$-$C_4$) alkoxycarbonyl radical, $R_1$ is a linear $C_1$-$C_{10}$ alkyl radical substituted with a cationic radical, said alkyl radical optionally interrupted with one or more oxygen atoms and/or with one or more NR$_6$ groups, said cationic radical optionally substituted with one or more radicals chosen from hydroxyl, $C_1$-$C_4$ alkoxy or $C_1$-$C_4$ (hydroxy)alkyl and the cationic radical is a linear or branched or heterocyclic radical comprising a quaternary ammonium —N$^+$RaRbRc, wherein Ra, Rb and Rc, which may be identical or different, are chosen from a $C_1$-$C_6$ alkyl radical which may be substituted with a hydroxyl, a $C_1$-$C_4$ alkoxy, or a $C_1$-$C_4$ (hydroxy)alkyl, Ra and Rb may together form a 5- to 8-membered heterocycle, in which case the Rc radical is a $C_1$-$C_6$ alkyl radical which may be substituted with a hydroxyl radical, a $C_1$-$C_4$ alkoxy radical or a $C_1$-$C_4$ (hydroxy)alkyl radical, said linear cationic radical is chosen from:

triethylammonium, dimethylethylammonium, diisopropylmethylammonium radicals, and mixtures thereof, quaternary ammonium —N$^+$RaRbRc, wherein Ra, Rb and Rc, which may be identical or different, are chosen from a $C_1$-$C_6$ alkyl radical which may be substituted with a hydroxyl, a $C_1$-$C_4$ alcoxy or a $C_1$-$C_4$ (hydroxy)alkyl;

$R_6$ is a hydrogen atom or a linear or branched $C_1$-$C_4$ alkyl radical;

An$^-$ is an anion or a mixture of anions which are organic or inorganic and cosmetically acceptable, with the exception of the following compounds:

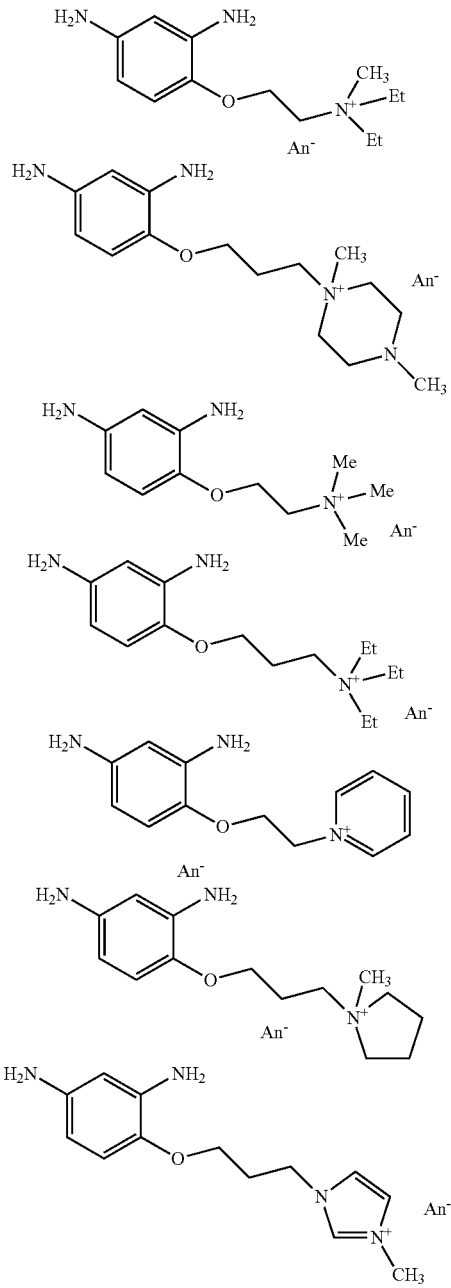

2. The compound according to claim 1, wherein R is a hydrogen atom.

3. The compound according to claim 1, wherein $R_1$ is a linear $C_2$-$C_8$ alkyl radical, optionally substituted with a cationic quaternary ammonium radical chosen from triethylammonium, dimethylethylammonium and diisopropylmethylammonium radicals, or mixtures thereof.

4. The compound according to claim 1, wherein $R_1$ is a linear $C_4$-$C_8$ alkyl radical, optionally substituted with a cationic quaternary ammonium radical —$N^+RaRbRc$, wherein Ra, Rb and Rc, which may be identical or different, are chosen from a $C_1$-$C_6$ hydroxyalkyl radical substituted with a hydroxyl radical or a $C_1$-$C_4$ (hydroxy)alkyl radical, or mixtures thereof.

5. The compound according to claim 1, wherein $R_1$ is a saturated linear $C_2$-$C_8$ alkyl radical substituted with a 5- to 8-membered cationic heterocyclic radical of which one of the members is a quaternary ammonium or a non-cationic heterocyclic radical substituted with a cationic radical —$N^+RaRbRc$, wherein Ra, Rb and Rc, which may be identical or different, are chosen from a $C_1$-$C_6$ alkyl radical optionally substituted with a hydroxyl, $C_1$-$C_4$ alkoxy or $C_1$-$C_4$ (hydroxy)alkyl radical; or mixtures thereof.

6. The compound according to claim 1, wherein $R_1$ is a saturated linear $C_2$-$C_8$ alkyl radical substituted with a 5- to 8-membered cationic heterocyclic radical of which one of the members is a quaternary ammonium.

7. The compound according to claim 1, wherein $R_1$ is a saturated linear $C_4$-$C_8$ alkyl radical substituted with a 5- to 8-membered cationic heterocyclic radical of which one of the members is a quaternary ammonium.

8. The compound according to claim 1, wherein $R_1$ is a saturated linear $C_2$-$C_8$ alkyl radical substituted with a 5- to 8-membered cationic heterocyclic radical of which one of the members is a quaternary ammonium chosen from imidazolium radicals, pyridinium radicals, piperidinium radicals, piperazinium radicals, pyrrolidinium radicals, morpholinium radicals, pyrimidinium radicals, thiazoliums, benzimidazoliums, benzothiazoliums, oxazoliums, benzotriazoliums, pyrazoliums, triazoliums and benzoxazoliums, the cationic heterocycle optionally substituted with one or more radicals, which may be identical or different, chosen from a hydroxyl radical or a $C_1$-$C_4$ (hydroxy)alkyl radical.

9. The compound according to claim 1, $R_1$ is a saturated linear $C_2$-$C_8$ alkyl radical substituted with a cationic heterocyclic radical chosen from the morpholinium radicals of formula (A), the pyrimidinium radicals of formula (B), the piperazinium radicals of formula (C), the cationic pyrrolidine radicals of formula (D), or the cationic piperidine radicals of formula (E) below:

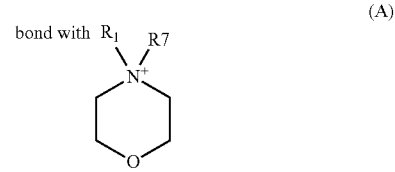
(A)

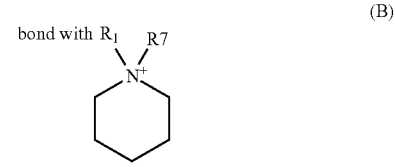
(B)

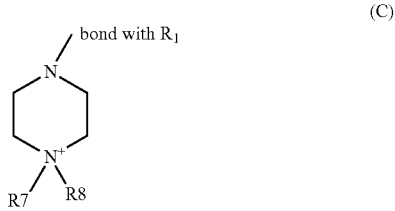
(C)

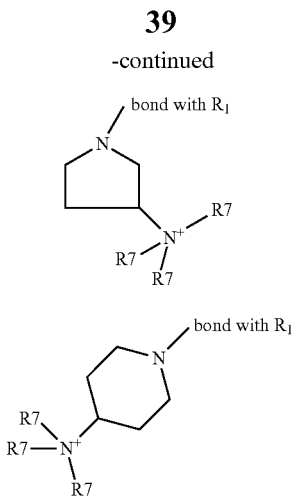

wherein R7 and R8 are, independently of each other, a C$_1$-C$_4$ alkyl or C$_1$-C$_4$ hydroxyalkyl radical.

10. The compound according to claim 1, chosen from the following compounds:
- 2-(2,4-diaminophenoxy)-N,N-bis(2-hydroxyethyl)-N-methylethanaminium,
- 2-(2,4-diaminophenoxy)-N,N-bis(2-hydroxyethyl)-N-ethylethanaminium, An$^-$,
- 2-(2,4-diaminophenoxy)-N,N,N-tris(2-hydroxyethyl)ethanaminium, An$^-$,
- 1-[2-(2,4-diaminophenoxy)ethyl]-N, N, N-trimethylpiperidin-3-aminium, An$^-$,
- 1-[2-(2,4-diaminophenoxy)ethyl]-1-methylpiperidinium, An$^-$,
- 1-[3-(2,4-diaminophenoxy)propyl]-1-methylpiperidinium, An$^-$,
- 1-[2-(2,4-diaminophenoxy)ethyl]-1-methylpyrrolidinium, An$^-$,
- 4-[2-(2,4-diaminophenoxy)ethyl]-4-methylmorpholin-4-ium, An$^-$,
- 4-[3-(2,4-diaminophenoxy)propyl]-4-methylmorpholin-4-ium, An$^-$,
- 1-[2-(2,4-diaminophenoxy)ethyl]-3-methyl-1H-imidazol-3-ium, An$^-$,
- 4-[2-(2,4-diaminophenoxy)ethyl]-1,1-dimethylpiperazin-1-ium, An$^-$,
- 4-[3-(2,4-diaminophenoxy)propyl]-1,1-dimethylpiperazin-1-ium, An$^-$,
- 4-[2-(2,4-diaminophenoxy)ethyl]-1,1-dimethylpiperazin-1-ium, An$^-$,
- 1-[2-(2,4-diaminophenoxy)ethyl]-3-(2-hydroxyethyl)-1H-imidazol-3-ium, An$^-$,
- 4-[2-(2,4-diaminophenoxy)ethyl]-1-(2-hydroxyethyl)-1-methylpiperazin-1-ium, An$^-$,
- 4-[2-(2,4-diaminophenoxy)ethyl]-1,1-bis(2-hydroxyethyl)piperazin-1-ium, An$^-$,
- 4-[2-(2,4-diaminophenoxy)ethyl]-1-ethyl-1-(2-hydroxyethyl)piperazin-1-ium, An$^-$, and the salts and/or solvates or isomers thereof, and mixtures thereof.

11. A composition for dyeing keratin fibers, comprising, in a medium that is suitable for dyeing keratin fibers, at least one meta-phenylenediamine compound of formula (I), the addition salts thereof and the solvates thereof:

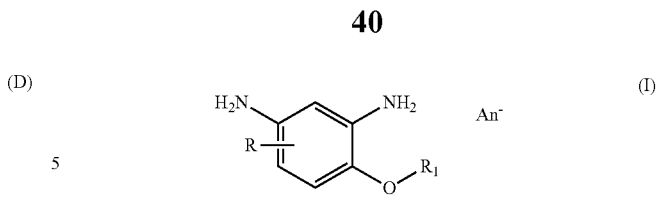

wherein:
R is chosen from a hydrogen or halogen atom; a C$_1$-C$_4$ alkyl radical; a carboxyl radical and a (C$_1$-C$_4$) alkoxycarbonyl radical, R$_1$ is a linear C$_1$-C$_{10}$ alkyl radical substituted with a cationic radical, said alkyl radical optionally interrupted with one or more oxygen atoms and/or with one or more NR$_6$ groups, said cationic radical optionally substituted with one or more radicals chosen from hydroxyl, C$_1$-C$_4$ alkoxy or C$_1$-C$_4$ (hydroxy)alkyl and the cationic radical is a linear or branched or heterocyclic radical comprising a quaternary ammonium, this quaternary ammonium being of the type —N$^+$RaRbRc, wherein Ra, Rb and Rc, which may be identical or different, are chosen from a C$_1$-C$_6$ alkyl radical which may be substituted with a hydroxyl, a C$_1$-C$_4$ alkoxy or a C$_1$-C$_4$ (hydroxy)alkyl. Ra and Rb may together form a 5- to 8-membered heterocycle, in which case the Rc radical is a C$_1$-C$_6$ alkyl radical optionally substituted with a hydroxyl radical, a C$_1$-C$_4$ alkoxy radical or a C$_1$-C$_4$ (hydroxy)alkyl radical, said linear cationic radical is chosen from:
triethylammonium, dimethylethylammonium, diisopropylmethylammonium radicals, and mixtures thereof,
quaternary ammonium —N$^+$RaRbRc, wherein Ra, Rb and Rc, which may be identical or different, are chosen from a C$_1$-C$_6$ alkyl radical optionally substituted with a hydroxyl, a C$_1$-C$_4$ alkoxy or a C$_1$-C$_4$ (hydroxy)alkyl;

R$_6$ is a hydrogen atom or a linear or branched C$_1$-C$_4$ alkyl radical;

An$^-$ is an anion or a mixture of anions which are organic or inorganic and cosmetically acceptable, with the exception of the following compounds:

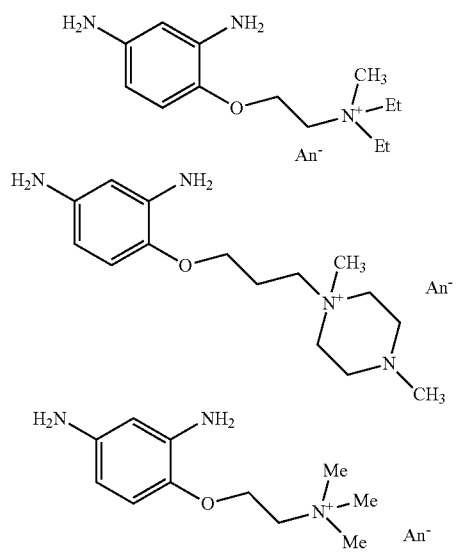

-continued

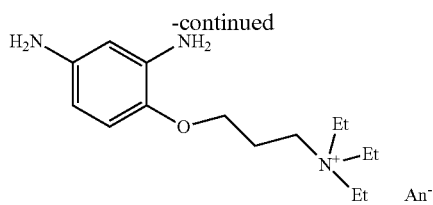

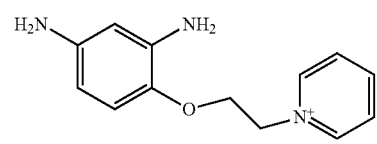

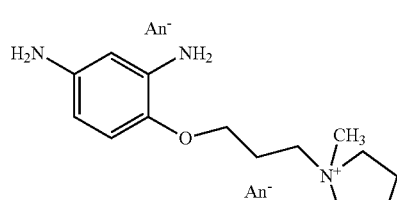

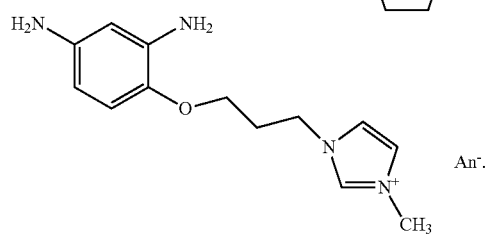

12. A process for dyeing keratin fibers, comprising:
(a) mixing, in a medium suitable for dyeing keratin fibers, a composition comprising:
(1) at least one meta-phenylenediamine compound of formula (I), the addition salts thereof and the solvates thereof:

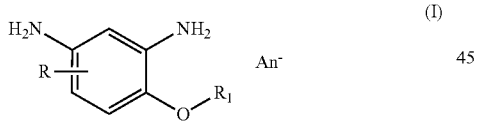

(I)

wherein:
R is chosen from a hydrogen or halogen atom; a $C_1$-$C_4$ alkyl radical; a carboxyl radical and a ($C_1$-$C_4$) alkoxycarbonyl radical,
$R_1$ is a linear $C_1$-$C_{10}$ alkyl radical substituted with a cationic radical, said alkyl radical optionally interrupted with one or more oxygen atoms and/or with one or more $NR_6$ groups, said cationic radical optionally substituted with one or more radicals chosen from hydroxyl, $C_1$-$C_4$ alkoxy or $C_1$-$C_4$ (hydroxy)alkyl and
the cationic radical is a linear or branched or heterocyclic radical comprising a quaternary ammonium, this quaternary ammonium being of the type —$N^+RaRbRc$, wherein Ra, Rb and Rc, which may be identical or different, are chosen from a $C_1$-$C_6$ alkyl radical optionally substituted with a hydroxyl, a $C_1$-$C_4$ alkoxy or a $C_1$-$C_4$ (hydroxy)alkyl. Ra and Rb may together form a 5- to 8-membered heterocycle, in which case the Rc radical is a $C_1$-$C_6$ alkyl radical which may be substituted with a hydroxyl radical, a $C_1$-$C_4$ alkoxy radical or a $C_1$-$C_4$ (hydroxy)alkyl radical, said linear cationic radical is chosen from:

triethylammonium, dimethylethylammonium, diisopropylmethylammonium radicals, and mixtures thereof, quaternary ammonium —$N^+RaRbRc$, wherein Ra, Rb and Rc, which may be identical or different, are chosen from a $C_1$-$C_6$ alkyl radical optionally substituted with a hydroxyl, a $C_1$-$C_4$ alkoxy or a $C_1$-$C_4$ (hydroxy)alkyl;

$R_6$ is a hydrogen atom or a linear or branched $C_1$-$C_4$ alkyl radical;

An⁻ is an anion or a mixture of anions which are organic or inorganic and cosmetically acceptable, with the exception of the following compounds:

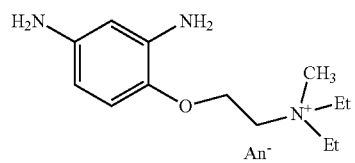

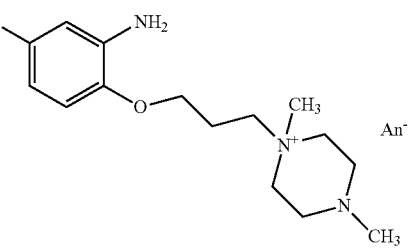

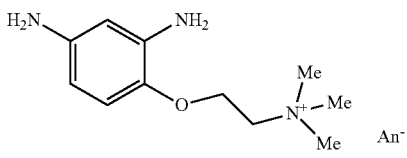

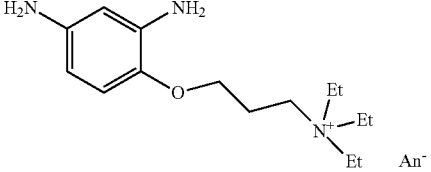

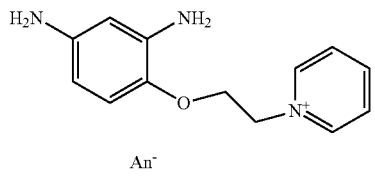

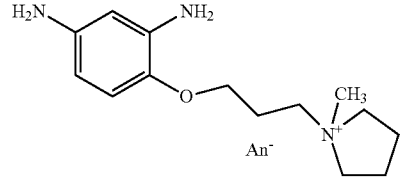

-continued
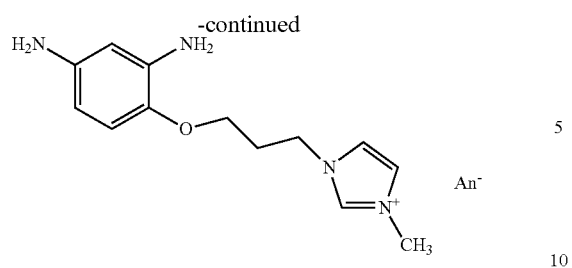
and
(2) at least one oxidizing agent; and
(b) applying the composition to said keratin fibers for a time that is sufficient to develop the desired coloring.
* * * * *